United States Patent
Yoon et al.

(10) Patent No.: US 10,898,531 B2
(45) Date of Patent: Jan. 26, 2021

(54) VIBRIO PARAHAEMOLYTICUS BACTERIOPHAGE VIB-PAP-5 AND USE THEREOF FOR SUPPRESSING PROLIFERATION OF VIBRIO PARAHAEMOLYTICUS BACTERIA

(71) Applicant: INTRON BIOTECHNOLOGY, INC., Gyeonggi-do (KR)

(72) Inventors: Seong Jun Yoon, Seoul (KR); Sang Hyeon Kang, Seoul (KR); Soo Youn Jun, Seoul (KR); An Sung Kwon, Gyeonggi-do (KR)

(73) Assignee: INTRON BIOTECHNOLOGY, INC., Gyeonggi-do (KR)

( * ) Notice: Subject to any disclaimer, the term of this patent is extended or adjusted under 35 U.S.C. 154(b) by 117 days.

(21) Appl. No.: 16/309,663

(22) PCT Filed: Jun. 13, 2017

(86) PCT No.: PCT/KR2017/006116
§ 371 (c)(1),
(2) Date: Dec. 13, 2018

(87) PCT Pub. No.: WO2017/217726
PCT Pub. Date: Dec. 21, 2017

(65) Prior Publication Data
US 2019/0160121 A1 May 30, 2019

(30) Foreign Application Priority Data
Jun. 14, 2016 (KR) .................. 10-2016-0073528

(51) Int. Cl.
| | | |
|---|---|---|
| A61K 35/76 | (2015.01) | |
| C12N 7/00 | (2006.01) | |
| A23K 50/80 | (2016.01) | |
| A23K 10/18 | (2016.01) | |
| A23K 20/153 | (2016.01) | |
| A61P 31/04 | (2006.01) | |
| A23K 20/195 | (2016.01) | |
| A61K 9/00 | (2006.01) | |

(52) U.S. Cl.
CPC .............. *A61K 35/76* (2013.01); *A23K 10/18* (2016.05); *A23K 20/153* (2016.05); *A23K 20/195* (2016.05); *A23K 50/80* (2016.05); *A61K 9/0017* (2013.01); *A61K 9/0053* (2013.01); *A61P 31/04* (2018.01); *C12N 7/00* (2013.01); *C12N 2795/10121* (2013.01); *C12N 2795/10131* (2013.01); *C12N 2795/10132* (2013.01)

(58) Field of Classification Search
None
See application file for complete search history.

(56) References Cited

U.S. PATENT DOCUMENTS

| 9,504,721 B2 | 11/2016 | Sung et al. |
| 2013/0323209 A1 | 12/2013 | Sung et al. |

FOREIGN PATENT DOCUMENTS

| KR | 10-2013-0087118 A | 8/2013 |
| KR | 10-2014-0000541 A | 1/2014 |
| KR | 10-1609111 B1 | 4/2016 |

OTHER PUBLICATIONS

Kim et al., Complete Genome Sequence of a Novel Marine Siphovirus, pVp-1, Infecting Vibrio parahaemolyticus, 2012, Journal of Virology, vol. 86, No. 12. pp. 7013-7014.*
Maje et al., Research Article Characterisation of *Vibrio* Species from Surface and Drinking Water Sources and Assessment of Biocontrol Potentials of Their Bacteriophages, 2020, International Journal of Microbiology, pp. 1-15.*
GenBank Accession # MT135024, Vibrio phage V05, complete genome, 2020.*
GenBank Accession# MN102376, Vibrio phage vB_VpS_CA8, complete genome, 2020.*
NCBI, GenBank Accession No. KM236243.1. Echeria Phage Seurat, Complete Genome. Nov. 8, 2014 (38 pages).
Surekhamol, I.S. et al., Isolation and Characterization of Broad Spectrum Bacteriophages Lytic to Vibrio Harveyi from Shrimp Farms of Kerala, India. Lett Appl Microbiol. 2014; 58(3):197-204.
International Search Report dated Sep. 20, 2017 by the International Searching Authority for Patent Application No. PCT/KR2017/006116, which was filed on Jun. 13, 2017 and published as WO 2017/217726 on Dec. 21, 2017 (Inventor—Yoon et al.; Applicant—Intron Biotechnology, Inc.) (Original—4 pages; Translation—2 pages).
KR, 20160073528 (101792522), Jun. 14, 2016 (Nov. 2, 2017), Seong Jun Yoon (Intron Biotechnology Co., Ltd.).
PCT, PCT/KR2017/006116 (WO 2017/217726), Jun. 13, 2017 (Dec. 21, 2017), Seong Jun Yoon (Intron Biotechnology Co., Ltd.).

* cited by examiner

*Primary Examiner* — Benjamin P Blumel
(74) *Attorney, Agent, or Firm* — Ballard Spahr LLP

(57) ABSTRACT

The present invention relates to a Myoviridae bacteriophage Vib-PAP-5 (accession number KCTC 13029BP) isolated from nature characterized by having a capability for specifically killing *Vibrio parahaemolyticus* bacteria and having a genome expressed by the SEQ ID NO:1, and to a method for preventing and treating infections from *Vibrio parahaemolyticus* bacteria by means of a composition comprising the Myoviridae bacteriophage Vib-PAP-5 as an active ingredient.

4 Claims, 1 Drawing Sheet
Specification includes a Sequence Listing.

[FIG. 1]
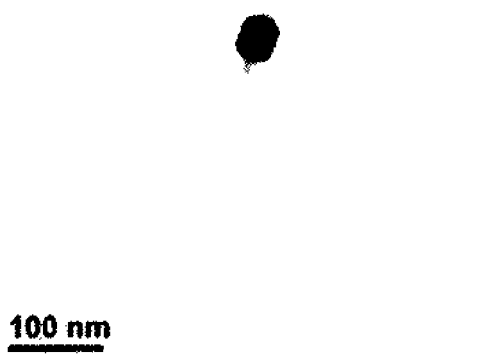
100 nm
[FIG. 2]
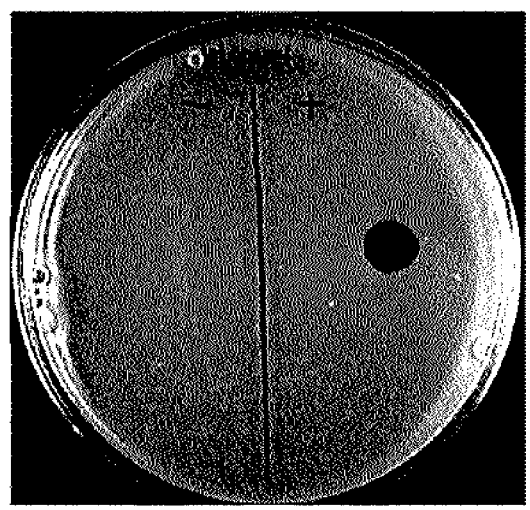

```
                        SEQUENCE LISTING

<160> NUMBER OF SEQ ID NOS: 1

<210> SEQ ID NO 1
<211> LENGTH: 58970
<212> TYPE: DNA
<213> ORGANISM: Artificial Sequence
<220> FEATURE:
<223> OTHER INFORMATION: Synthetic construct

<400> SEQUENCE: 1 gcttttatg gaggccggag atgccgcatc gattatttat ttcctcagat atgtttcacc       60
ctgtatatac atacagtatg accgatgtac agcttatcga tgtgtgtaca gctttgaggg     120
gtatatcata ctcttcggtg tacatagggc gatgacctgg acgtgccgcc ggggcccga     180 tgatcgtcga caatatatgt cggccgagat ggtgacaact ttatccgccg tccaaaaaga    240
tttgaggttt tagaatgttg tctagtaatg tgctgcacac tttgtataat gtacatactt    300
tctgcaacaa cataaggtct acatgatgga aatagctaac gaagaagtgc ttcaatacat    360
tgagtggtat gaagcaacat accctgaata tgatcagtgg acgtgcactg caatcaaaac    420
atggatcctt aacaagtaca acgtgtcgca agagaacctg tctgtgtacg ctgagcaatt    480
caaccgtgtg cgcacactgt ggtcacaaaa gctcaatgag caccgcctta acaaggggtt    540
cccagaatac ttcggcattc acccgttctt ggacatgtct aagaaatact tcggtattga    600
gctactgacg gagcctggag acgaagaaaa ggtttacgca cgtattaaca ttgagcgtaa    660
agagttcatt gattgggtta agaaggagtt gaccacatgt ctgtcgtaat tagcaccgct    720
cccactattg ctgccgctac tgttgcgcta aacaacacgt ctagtgatat accgcctgaa    780
cttggtatac tgcaattctt ggtatttacg ccgcttattt ggttctgcgt gtgggcaatt    840
ggcgcaacgt gcgaccgttg gttctggcgt tggttttggc acgctggcgt tggatcgctg    900
agcttaatcc ttgcaattcc attttttactg gcattggacg tgctaggtgt accgcgggca    960
atgtacctcg cagaacgaat cgttaaaaca ctggaaatac tacataatgc actctttacc   1020
taaagcagct tcaatgtgga agcgtgaaca gtacgaagaa gctactaaag ctgtacagac   1080
aatgtttaac catattaaga agtcttctga ctttacgtat ggttttgaat acgcgtttaa   1140
aggtatgaat gcgcgtattg ttgtgtcgga tacttacttc acattagtgt gcggcgataa   1200
ccgacattcc gttccccgta acaaagacgc ggggggttgtt actacccttta cgggacgtta   1260 aacatggcaa tgagtgtttt acaggtgaaa gtatctgtta tggatactga accaatgagc   1320
gagttgatct caattatttg tggttgggat cgtgataagc ttccggttga gtacaaagac   1380
caactggaag gatgggcaga caaattctta gatggagaac cagatgaacc tgcaaagcct   1440
ggaaaagctg aacagcttgt tgaagcagca cgaagcactt ctacagaaga ttaaaaccat   1500
tcgcgacatt gacatcgagt ttggttttat tcgacgtatt gatgggcatg accacataca   1560
cggcaagctt cgcaacgagc caaagctgac agaacatgtg gtcaatttct ggcatgacga   1620
agcttacgaa attgagaagc agttggaagc tttgggcttc gacgttacgt ccttagaggt   1680
gcgttgcagc ccgccaccgc aacctagcgc tgagtaatct agcttttgaa cgttccaagc   1740
ggtatattaa cactataccg cttttattgt atttaaagga gttagtatgt caaaacgaat   1800
tcaacgcgct aagaaagcaa tggacaactt cagcgcacgt ggtagcaaat gcccaatctg   1860
```

```
caaagcacag tttagaacgg gttgcaacca ctcggtaaag caagcggaag aacgcttatt    1920
ccagaactac gtaaaagcaa ttgcggaggg taaataaatg aactgtacta aatgcaactc    1980
ggaaaacacc acaacctgtc gtgcaactgg tcacattatt tgcagaaact gtctctacat    2040
taagcgcgac cacttctcac tgtgcgagca ggaagttatg cttgagcttg aaaagcaaga    2100
ggagcaagca atggaggaat tcatccaagc taagcgtgga gaaatgaaac tcgaccgaaa    2160
gaccgagctt gagcaaatgt ggcaaacgca acgtgctgaa agcgaaccaa tgggcgcaac    2220
aacccgagca atgttactca acgggcagtt tggtaagcat ggttcaatcg ataacaagtt    2280
ctacgaagag cttgctgaac gtaacaaaat tgcaattgca cacatcgaag gtagtgcaga    2340
atcagctgcg caagctttcc gctcactagc taccgcaatg gagaagtgcg ggcatgagtt    2400
agctcagttt gcttatgttg tgaccacaga ggctcgcgat aaccttgtgg cgcaaggtta    2460
ctctccagac atgttcattg ttagtgacag cttcccggat attagtgagg tgcttcctcg    2520
cggtggtgaa gttgtgatta tgggtggtcg cggtggtggt aaaagtggtc ttgttgctga    2580
gttactgaag tgttctattt gtccaaccca taaggtgaaa gcgggtcagt taggtggtcg    2640
cacatccaaa ggagaccgtc gtcgcaaacg tcaacaatgg aatcgcccgc gaggtactaa    2700
ctaatgtttg actggttacg agcttggtgg tgtactcact tcgttgagac gcccgcacgc    2760
gagagtgttt ggtattcaaa cagacacaat tctcgcattg ttatagttga ctgtgatggt    2820
tacaacgtat attacaagtt cgtaaccatc gacgggaagt ctgcaactag cggtgacacg    2880
tacagcgtag ctttatggta tatccgcaaa tactataagg aggttcctgg tcttgcaaaa    2940 gggagctta gagcatgacg tgttctgcag cattgttacg ctaaaccgct ttacatacgc    3000
tgaacttagc tgtattatgg gtgttagttc agcgcgctta aagcgtgcaa ttaagtctct    3060
tagacaaaag ggcgtactta ttcaaacaac tggtggtggc aagggttcca aaatggaaca    3120
ggaacgcttc cttgaatata aaggacatct accacctaaa caaagagag gattacatgg    3180 caaccctaac tgaacttcgt gtaaagaaac tgcaagataa agttcgcaac gctcgtgttg    3240
aaatgcaagc tgcggaagag tctttgcaat atgcacgcgc aatggaagac ggtcaaacta    3300
ttaatttagg ttccgcaatt ggtagctttg acatgtctaa agaacagcta gttgcagcag    3360
ctgagaaaac gtacaaggaa aagaaaggtc gttacaatgt aatgtgtaac ggtgttgata    3420
gtttcctaac tggtatgggt atagaactat gattcgtgtt tataagcgta attggttcgg    3480
tatgctgaag tgcattgctg agttcagcga cacctattac cgcattgttg ttagcacggg    3540
tggggtgttg acaattcgtg cagcaaacca ccgcgaaaca accattcttg cactagaacc    3600
taaagaatgg tctattgcta agtggaggga taagtaatgg ctaaagtgac cacaattgtg    3660
tgcgacggtt gcggtgaacc tatcaccaaa gaacgtgaca atgacagcca agcgttaatt    3720
cgtttggttt acccaagtaa gaaccatagt ggtttcgaag ctatggaaac aaacgaccta    3780
tgttccgcgt gttactgtaa agcacaaagc gcggtactgg aaatccttaa acctcaagcg    3840
tggacccttc accctgatgc gcgcctcatg ctagacgtga gtaatgtgg tcatgcactt    3900 tccaattgaa gactttatta aaaatcgtcg caaggaacta gctgacggtg aacgttacgc    3960
tggcaaccaa ggtgttcgca agggtaagaa accaaccaag aagcagattg atgctttgca    4020
agcgggtcat aaagcgttgc gtgagaagcg acttatgcaa catgaagtta agcgaagtaa    4080
gggttaaatt atggcaattg taaacgaaaa gatgaagcgg ggctttgaag agctctaccg    4140
cattggtgca actgcaaacg tattgcagaa cttcatgcgt gaagatgttg actacactta    4200
cagcattgaa gaccttcgtt caatggacga gctcagctta gagtgtcgaa acgggttcaa    4260
```

```
ccttatcaaa cttggtatgc aagaaattat ggttaagcag gaagagcaca tcgagtttct    4320
tggtcgtaag ttaactaagg gcggggagt gcgcttccct aattcggaag cgttgttagt    4380
tcgtttgaac gcgaacaccg accgcgttgt gtgggagttg acacctgaca cttactatcg    4440
tatgaaaagc gagctagagt cgaaaggctt tccatttgcg attatccctt gcggaactgt    4500
agcggataat ggtacaacta ccgttacaca aggagaatca aatgacgctt aaaccgattg    4560
accacattac acagccgtgc ggacgctctt gccaaagtgc ctgcctcgcc atgcttacgg    4620
gtcaacctgt tgaaaagcta attgaacgtc atcacgcgga cttggagact ggtaatcgcc    4680
gtttccatga agtgtgtgag cgttatggtg tggttgttga aacgcctgac gaccttgaaa    4740
acatttttgc ggggtcaatc tatgtattga ttgtgtcgag tggtttacta accgaattgc    4800
acatgatcat tgtagatgca agggacgctg agaatatccg cgtttatgac cccgcgtcca    4860
attggcgtca atccattaac ccgcaggaaa atgaagtgaa actccgtgct tttgttgttc    4920
gttaccgtgt tgttctagct ccacacttgg gggtgctata atggttcatg ttgtgaataa    4980
aggtaaggaa gggagcgcg agtttatcaa gttcctgcaa ccaatggttg acgaagtata    5040
cagcaagcta ggtttagaac ctatcaagct gtttcgtaac cagaaccagt cagctctggg    5100
cggttacgat attgacggga ttccttggtt agctattgaa attaagcgtc aagaagcgct    5160
cagcatcaat acgtggtgga accaagtgct gaaagctacg ggtgaacacc aagtaccgct    5220
attagcgttc cgtcaaaacc gccagaagtg gcgctttatg gtgtggtcac acatccatac    5280
aggcggctct ggctacgttc aagttcgttc agaacttaac aaggaagact ttgagcgttg    5340
gttcaaagcc cgacttgctt atgaagcagt tcaggaaggt ggtgtatgat taatgtgtgg    5400
tatctattcg gtactgtagg cgcgttatta gctgtactcg cttatttcct agttgcctca    5460
tcccttggga atgctactgg tgaacgttac aacctttgta acctaatatc cagtattcta    5520
atgggactga gtttggttgg cgctgctgac caacgtgcac tagttgtaag cgtgggttgg    5580
atggtggtga gcttatatat gctctatcgc ttgaagcgtg aaagggtaa gctttacgtg    5640 tttgattggg taacacgttt gcgcccaaaa tagctaaaat aagtcttgca tagaattgtt    5700
ccttacatta ttataagggt gttgcttcgg taacacccct ttttattat tctgcaaagg    5760 acatgaacta tgtttaagcc gatgttagct gcaacagcac agctagacgc actaaatgaa    5820
aacttcttcc aatcaattaa gcttgaaggt gtacgcgcac agttcacacc ggatgaaggc    5880
ttagttaccc gccagttgaa accattcaac aacacaatta tttacgagcg ctttgacgcg    5940
gttgagcgtt actgctatga ccacaatatt atgctcgaag gtgaattcta cgttcacggt    6000
tgggacttta agcgtattga tagttgctgt cgtggtgaag gtaatattga cgcacgccaa    6060
atggagttcc acgtgtttga ctgttgggat cccgagcaac cagatctacc gtttgaacaa    6120
cgttacgagc tttataagca acacgttacc gcactgtgcg cgcttgtggg ccacattgtg    6180
cacgctgtaa tgcaataccc ttacgtaagc gaaaacgacg ctatgcacgc ctacgggtgg    6240
gcaatagagc acggttatga gggtctttgc tttaagcgca aggatctagc gtacaaactc    6300
ggacgctcca ctgttaaaca gggttacttc ctacgcatca aaccagaaaa cccatatgac    6360
ggaattgtgt tagggtttat cgaacgacag cacaacctaa tggaaagtga aaccaatgag    6420
cttgggcagc ttttcaaacg tcaaaacaaa gacatgaaac gtgctgcggg tatggttcaa    6480
aatgcgttgg tgtacacacc tgaaattgat aagatccaca aggttgcaat gacacgtgga    6540
cttacagacc ctgaccgtgc aatgctgtgg gatacgcaag atcaatatat tggttgcgga    6600
```

-continued

```
attcagtggg ttggtattcc agttccagga caggacattc cacgttcccc gcgctttgac      6660
aagtggcgac acgacattca accaacgttc ctcgcacacg atagtggtgc attaatggtt      6720
gaatgggatg cggacaaggt tgcaagttac ttggaaagtg cttgtgacgc catagacttg      6780
accacattct tggagcgtgt tgcgagcggt gagtggcaac tcggtaagta gaagtctaag      6840
gtttattaat agcatagttt atttgaatta actttgctat tagttgctta taccacgtga      6900
agccttgtta gtaatagcaa ggcttttatt ttgacctaaa gatgggtctt ttgcaatacc      6960
ctagctttta aaattcaaat gtggcattat caaagagtaa ttcatagact tattgtttgc      7020
tatagttgaa tgcggtttac caatgccggg atgacccgta tagcgaatag agcaaacttt      7080
attaaaagaa cgtactgcgg gcagcaatta aacttgtgtg tgcacaccaa aaaagcgtta      7140
taaaacaagg gtttaagggc gaaaaagggc aagtgtgcaa gtgcgccagc gaggtaggcc      7200
tattttgggg gatcctttgc tgtgcacttt gcacacttgt ttctgcttaa acacttaccg      7260
acataaaagc aacaactagt aaaacataga atataaaata aaagcttata acgtaataaa      7320
taatatatcg tgtgttaat ataaaggtct atttgtttta aggaatagtt tttaattcgg      7380
attagggtgc atgtctatat tgaacaaaac cacagtagtg ggcaaatttt ctgcgcaatt      7440
aggggtaagt tgcgcaatga acggttttgt ctatgctttt gcaatagaaa tatgtatagt      7500
tacaacataa agcctatggt ttacccgtag ttagcgcgag ccacaatacc ggcagcgaca      7560
cacggtgcaa ccgtaacacg tggtcaccac atttaaacag ccactttcgg gggtgctacg      7620
gggttttaac aacggatcgg tgcagttgta ccggcaacat taacaaagcg gcccacaggg      7680
gcttacaggg gtttagaatg gtagctgtaa cgctaaaaga accaaaagca agtaacaaca      7740
ttattacact acgtgaaact attcaatttg gacgcttccg tggttgtact ggtgcggaac      7800
ttatgaaatc tagtgatggt acttcctacc ttgtttggat ttacaacaac acagacatcc      7860
aaattgaatc ttcaattgtt aacacactag ctgcgcatgg tttggtgaaa cttgacgctg      7920
ttcgtaaaaa ccagaaagcg ggtggcgttg ttgaacctga gaaacgtaca cctgttgatt      7980
gggcttgtaa agctcaaatt atggttgacg ctgcacgttc cgctgcacgt ttggaacact      8040
gcgttaaaga tagtgttcca attcgaactg accgcgaagc gggtggtgtt atcgtagtta      8100
atacgaaagt attagaacca gatgagcgtg agcgcatctg tcgcaagttc cgtcaggtac      8160
ttaaacgcga gacagaccgc atgatgcgtg atattgttat gtagcttta gaatatgcaa      8220 ccgtttacaa aagcaaggcg aagtccttgc tttttagtg agcttactat accattatct      8280
ggactgtaac catttctgag gttccatgg acgccactac actaatgaca gggtctaatt      8340
acatggatcc gtcagagaaa cgagagcttg atgcttttat tgctgagtac atgaaggact      8400
acgattccta tcgtgctact cttcgcttaa actatgatcc agaggttgcg cttgagcgcg      8460
ccaagcagtt ctgggatcac ccttacgttc aacaatgcat taccgaaata caagagaacc      8520
gttctgcact ttggaagcag aacgaccaac gagatcttag tcgtataccg gaagactttg      8580
ttccctctga tgaagatttg gacaaacagc gcattgtatc tgcactgttt cgcgaggcgt      8640
tctatcgcgg tccaggctcg acgcacagtg cgcgagttgc tgctttgagt aagctttccg      8700
ctatctacaa actagagaat gagaagcctc ctgaagcaga cggacgttcg gtaatggttg      8760
tgcctgccac tggtaacttg gatgagtggg agaagggtgc agcgaagcag caagagaagc      8820
tcaagcaaga ggtaaaacta tgatcccaag gcgaataacc gttcattgta gcggttcccg      8880
taaaggacat tcgatgaccg tacaagagat tcgaaattc catacgtccc cgaaaccgca      8940
tgggcgaggt tggtctgata ttggttatca ctacattatc gaccaatatg gtaacgttca      9000
```

```
cgatggacgc cccattactc gccaaggtgc aggtgtaaaa ggacataaca aagacactgt    9060
tcatatctgt ttaattggcg ggttaaatag tcatggtgag cctgcgttca cttatactga    9120
ccctcaaatg gaagctctgt ttaagcacat tattacgctt gacgagcaat acgacaccat    9180
ccgcttggag gacacacgtg gtcatcgtga ttattctcca gaccgtgatg gtgatggtaa    9240
aattggcccg cacgagtacg tgaaagcatg tccatgtttt gatgtgcgtg aatggcttgc    9300
tgcgggttta gaagctcacg gaatggttta atggcacagg aaaaggttac agtcgttgag    9360
gcaattcttt tcagtggtct tgctggcgta ggtggtgtgt tatcatactg cctacgtcag    9420
gcaaacaaag gaaagaaacc cgctcttggt cttgcactac ttgaaggttg ttcttccgcc    9480
ttcgtcggtt tccttgccat gctaatgtgc aaagctacag gattggattg gtattggtct    9540
ggtgttgtgg ttggtgtgtt tggttggttg ggtgcgaacg cgagtattgc agttcttgcc    9600
aaagttgttt acggaaagat aggtgttaag ggtaagaccg atgatgctaa caaacattcg    9660
taaatattta actataggt tggcactagt tgccacccctt accattattt acgctgctgt    9720
aactcagtcc cgcttaaaga gtgcgaagct tgttattaat tctcttaacg gggaaattga    9780
acttttgcaa aatgcagctg aggtgaatga aaacaccatt gctattttgc gtgagaatga    9840
caagatgaat cgtgagtacc gcgaaagtct taaagtgaag tttacagagt tggagctaaa    9900
ccatgcaaag caattgcgag aagctaaaac gttcattcct gagtctgact acgcttgtct    9960
taaccgtgtg catcctgtgg aatacgggcg gatgttccag cgtgaaaacg gtggtggaaa   10020 cacgacgat cgttctaaaa ccggacgctg agttacttga tgtttgcaat gtacctgagt   10080
atcatggtac aaagtatata gacatccacg acttcgcggg ggaactatgg ttagccctgt   10140
tgaagtgcga agcccgcgat aaagaacgat tagaatggta tgaaaaacaa gaagaacgta   10200
ccggacaacg ttaacgtaat ttggaaacct cagcccggct cccaacagtt agcgattagt   10260
tgtccgtgta accacatctt aatggaaggc acgcgaggcg gcggtaagac tgacaaccaa   10320
gtcatgttct tccgtcgctt tgtgggtttg ggttacggaa gttttttggcg cggtgttatc   10380 tttgaccgag aatacaaaaa cttggatgac ttaattgtta aatcgcaacg ttggtataaa   10440
cagtttaacg acggtgcaaa gttcctgaaa ggtggtggtg actacaaatg ggtttggcct   10500
actggtgaag agctgctatt ccgtcagatg aaaacggaag acgattactg gaaataccac   10560
ggacaagaat tccatttat tggatggaac gaattaacca aacaaccgaa cggtaactta   10620
tacgaaatga tgatgtcgtg taaccgttca tcctttctac caatggagca tacgccacgt   10680
caccaattga cgtttgacga tgaaggtaac attatcgacg ggcttctacc tgaacttcca   10740
ttggtagttt tttctacgac taacccgtat ggagttgggc ataactgggt gaaacagcgt   10800
ttcatcgacc ccgctcctcc gggcgtggtg gtacgtgata ccaaagaggt attcaaccca   10860
cgtacacagc gtagggaaaa catcactaaa acacaggtac gattgttcag ctcgtacaaa   10920
gagaaccgtt acctgtcacc cgaatacgtt ctggagcttg agtccattac cgacccgaac   10980
aaacgtgctg catggttgga aggttcatgg gacattacgt ccggaggtat gttcgacgat   11040
gtgtggtcaa gtacacacaa tatagtggaa ccgtttagac cgcctgaagg ttggcgtatt   11100
ttccgttcat ttgactgggg ttcgtcccgt ccgttctctg ttggttggtg gatggaaagt   11160
gatgggtccg actacgttga tgccaagggt aacattcgca gctcaatccg cggtgacgta   11220
tatcgcatcg ctgagtggta cggttggacg ggtgttccta acgaaggttt gcgattactt   11280
gcaacccaaa tatccaaggg tattgttgag cgtgaaattc gttggggtat taggggtcaa   11340
```

```
gttaagccgg ggcctgcgga tagttccatt tgggacgatc agaacggtaa ctgtattgca   11400
acggacatga aaaagcgtgt tcgtattgac ggtaagcaat attctggtgt tacttgggaa   11460
cgtgctatta agtctccagg ctcacgtcac aacggttggg aaatgatgcg cgttgcaatt   11520
gtcaacgggc aaccagaccc tgacggtttc ccacgtgaga agccaggatt ctttgtgttc   11580
cgtaactgtg accaattcct acgaactgtg ccacctattc cgcgcgatag caaggatatg   11640
gacgatgtgg atactgacgc agaagatcac attgccgacg aagcccgata tgtggtacta   11700
tctttgggca aacgctttaa agttaagaag actactggtt actattaagg ttcacatatg   11760
agcggcacta agcgcaaaat aaaccatcac ccactgtaca cggctatgtt gtcggtttgg   11820
acaatgtgcc gtgactgtga gggtggttcc cgcgttatca aatctaaacg cgatacctac   11880
ctaccgccta cttctggtat gcttgcggat gggttctcaa atactaactc gaatagtttg   11940
ggttctaagg tttatgaaac ctatattacc cgagcttatt accctgacgt gtttaaagat   12000
gctgtggaaa ctgcggtagg tattatgcac cgcaaacctg caaacattaa actcagtcca   12060
aagcttgagc aactgcgaga ccgtgcgtcc gatggtggtg aaacacttca actactgtta   12120
agacgtatta acgcggaaca gttaacaact ggtcgacttg gtttgatggg tgacattcgc   12180
gttaagaatg gtaaagaaga gcctgttatc ctagtgtaca aggagtcaac tgcatacaac   12240
tgggatgata gttcgcgttc gcgtgcggat tctaacttgc gctttgtaat gttagatgag   12300
agttcttacg agcttaacga ttcctttgca tgggtgtgga aggaaaagtc gcgtgtactt   12360
gcactggtcg accctacaac taagcgtatt gcacaattgg atgacgacgg taaaattcct   12420
gataacgctg tgtacggtta cgcagagatt gaaagcgacg atgagttagc tgaaaaagaa   12480
tttacaattg taagcgttaa gggtagcaat gttgatggta ttgcgttcac gtttgttaac   12540
tcacgcgacc tattgtcaat tccggatacc ccaccgcttg agggtcttgc tgacctgtcg   12600
ttgcttattt accgtggcga agctgactac cgtcaaaacc tgttcatgca gggacaggac   12660
acccttgtta cgatcggtga cgttggtggg gaggatgacg acggtgacgg taagacaact   12720
cgtacgggtg cgggtgctcg tttagctcta ccagttaacg gtgacgcgaa atatattggt   12780
gttgactcac aaggtttacc tgagcagcgt caagcacttg aagctgacta aagcgcgca   12840 gagaagaaga cgtccaagtt gatgtctggt actaacacgc aggaatcggg tgacgcactt   12900
cgtattcgtg cagcttcaca aacagcaaca cttccacaaa ttgctcagtc tggtgctgcg   12960
ggtctacaat acatccttcg taagcttgcg caaatgctcg gtgacaaccc tgaagacgtt   13020
gtggtcacac cgaacatgga gttcaccgat aaaggtggca accctgtcga ccttaaatct   13080
attatggaag cgaaactact tggtgcacca attagtatcg agtctattca tagctggtct   13140
aagcgttctg gtttcactga ttacgattgg gaagaggaac agaagaagct tgctgaagac   13200
gacaaatacg acttgtcgtt tagcactggt aacgaagatg aagcaacgtt gaacgttggt   13260
acaaacattg acattaataa tccggacgac actggtaaag gtacgcgcga cggagtagat   13320
gacaatggcg acgtttaacg agcaacttca agataagctg tggttgcaca gcttatacgt   13380
tcagcgctac gcggcacgct taggtcgttt gggtaatgat cgtatactta ccactgagcg   13440
cgaaatacgc gctcttataa ccgagtacgt tgcccgtatg gacggcgtac caattaccac   13500
taagcgcggt cagcaacttc ttaaagagtt tgaacgcaag ttaattgaat tgcgtcgaaa   13560
agcgtgggtt gagctcacag ctgaacttga aaaagaagca aagcagtttg caaaagttga   13620
ccacgctgca caaattaaag tggttgacga cattatgccg cttgctattg gtatgcacgc   13680
gctagatgtt gcttccatta ctgctattgc gacggtgcaa cctttcgagg gtaacacgct   13740
```

```
tcgcggttgg atgacgcttg ctcaacagcg cgacattaac cgcctgcttc gtgttgctcg   13800
tattggtatg gtcaacggtg aaaccattga gcaaatggtt gcgcgtgtta ttggttcaca   13860
gaagtatcaa tacaaagatg gtatgtcgcg caagttccgc tccgatattg aagctaattt   13920
aatcacctgt attaacggta ttagcaacaa cgtatgggcg aatcttgctg ctgctaacga   13980
cgatatcatt gattacgaag tgttccaggc tacactggac ggtagaacta ctattcagtg   14040
tgcgagtaac gataacaaga aatttaaggt gggtgaaggg ccgatacctc cgcttcacat   14100
gcgatgccga tctaagcgtt tacctgtggt cacagatgca gcgttcaacc gccgtggtat   14160
ggatccaaca tttgaaaaag aacttgtgca agagtttgct cgcaaaaacc aacttggaca   14220
agttaataag gttggggact tgccttatgg gtacaaaaca gcgtataata agtggatgcg   14280
ccaccgccgt cgtgaattgg ttggtgatgc gcctgctgac ttgcgctttg aagattggct   14340
gcgtaaacgt agcacagctt ccaggatga gtatcttggt aagcgcaagg cggaactttt   14400
ccgtcaaaac aaattgtctt tggataagtt cgttacccgt gacgggtatg agttgaccat   14460
tgaccaacta gaaaaattag tttcctaaga gagcatgggc tcgggagtat ataaatgaaa   14520
cgtacactat tatcgcacgc tgtgatggca caggttgcac ttctgtcttc taaaggttac   14580
ggtgaagacg acatttctct aatgacgtct tacaacgcag tggatgagat tccagaacct   14640
ttccgcggtc tgtatactga acaggacggt aagcacgttc tgtcaaaagt tgttggtctt   14700
aagacacaag acgacatcaa ccgtttgcaa ggtgcattgg acaaagagcg taacgaccac   14760
aaggctgtga agggtgcact tgcgaagtta ggtgatcgtt cgattgacga tgtacttacc   14820
atccttgata aggttccagc ttgggaagca cttgaagcac agagcgatcc gagtaagatt   14880
gacgagcttg taaacggtaa gctttcgcag cacactgcac cgctacagcg ccaagttact   14940
gagttaacta ccgagcgtga cggttacaaa gagaagttcg aagcgctaca aacacaagtt   15000
aagacagata agatccgcgg tacgttgaag gacgctgcgc ttaaagctaa agcactgcca   15060
gaagctgctg acgacattgc aaacatgggt ctaggtttgt tcgatgtgga cgacgcgggt   15120
aatgttgtgg tcaaagcgga tgctaagggt gtcactccgg gcattatgcc tgaagtatgg   15180
ttaaacgacc tgaaagacag caagccgttc tactggcctg catcgcaggg cgctggcggt   15240
caaggtggtc aagtggtgg cggtcaaaac aaccttgga agcaagagac gctaaaccta   15300
acagagcagg gtaaacttgt tcaaacaaat ccagcgttag ctcgtcaact tgcacaagct   15360
gctggcgtaa ctccaacatg gtaaaatgaa ttgttgcatt gacaacaatt atccattata   15420
tttaagggac tgtcatgggg cagtcccttt tttacgttag cggccatggg gtacgcgaca   15480
ttatttcgtt aatacgccat aatagaggag atatcctgtg gctaaactga atcctattct   15540
tcgctcaatt ggtgcgggtg aatctggtgt tgtacgtcta gcggacgtag ttgtacctca   15600
agtgtttacc ccttacgtac agcaacaaac agaagaaaaa tcacgcctaa ttcaatctgg   15660
tgtgttggtg cgcgatgcgt tcttggacaa cttcctagct ggcgcgggcg ctaccattaa   15720
cgtccctggc tggaaggact tggataacga cgaagagaac tactctaacg acgacccaag   15780
tgcaaacagc actccaaaga aaatcggtac tgcgactgaa gttgcaactc gaatgaaccg   15840
taaccaatct tggagctcaa tggacttgac tgcgcaactt attgcgcgtg atccaatggc   15900
tgcaattggt ggtcgtgtag caaactactg gacacgccgt atgcaagcga tgttcattgc   15960
taccgttcgc ggtgtgtttg cggataacgc tgctgatcct gtttcaggcg agcacgttaa   16020
gaacgacctt acccacgata tttctggtac tggtgcagct tctgcgacaa ctcgtttcaa   16080
```

```
cggttctgcg ttcattgata cgctgaccac aattggtgat agtgaagacg atctaggtat   16140
cgtgttcatg cactcaatcg tgtatgcgcg tgctaagaaa aacaacctta tcgactttat   16200
ccctgatgca actggtaagg tgaacatccc gacttacatg ggtcgcactg ttattgttga   16260
tgatggtcta acgtctacaa ctgctggcgt gtacgaaact tgggtgttcg gtcaaggtgc   16320
attccgccta ggtgttggta ctccagaagt tccaactgaa gtggatcgta aaccttctgc   16380
gggtaacggt tcaggtcaaa ctgttctgca caaccgtgtt gagtggtcta tccaccctgt   16440
gggccacgct tacacaacca ctccaggcca gtctggtcca actaacgcac agttggcgtc   16500
tggtgacaac tggaagcgtg tgtacgcaga gcgtaagatg attaagatgg cacgtctaat   16560
cactcgtgaa gcttaattca caaccgaggg gtctttgacc cctcaagttg gagtaccaaa   16620
tgaaacaagt aattttagat gcactagcta aagttgacgt tgagaatgac gatcattgga   16680
ctgctgatgg tgctgttcgc gttgacgtag tttctgagct tattggtgaa gaagttacac   16740
gcgctgatat taccgcagcc gctccaaagt ttaaccgtaa gaacacggaa cttgctgacg   16800
gtggtgtggt ggttgctgag tctacaaccg aacctgacct acctgttgac actggcaacc   16860
aagttgcaga agacgacgca aaaggtgacg gtgaaatccc agaaccgcag tttgcgaacc   16920
cttgggaaaa agcagcaacc gaagcacgcg agtcaatggt taagcaggaa tttaacattg   16980
gtgagacgca agaagcaatt gcggaactaa cagcgttgcg caaggactac gttggcaaac   17040
gtgtggtcat tgatgctaag atccaggaaa tcgacgaaga agttcaccgt ctaagtcagc   17100
tttgcaagca accagaactg tcgcttaaag agcagttaga tatggttcta gcttctgaag   17160
cgggtgaagt tgaagaacgt gaaaaacgtc gtaagctaat caaagagctt atgaacaatg   17220
ataagtctat gcttgacggt cttgacatgc ttgactaact ggagataact atggcgataa   17280
agcgcggtgt taagggtatt aaaagacatc acccaatgaa cggtttacgt catccaggat   17340
ataaattagc ggcgggtcaa tctcgccgct ttattgcatg gtccgtacag cagaatgatt   17400
cggtcaatga tgaacctgtt gaacctgttg agctggttgt tgatggtgac attgtataat   17460
actgacaacc ccttataatg gggttgtttc gttttttggag gatttatggc aattactgtt   17520
gaaactggtt ccggtgttgc gggtgcagat tcttacatct ctgttgtgga agcggattcg   17580
tacttcgcac gatttggcaa cacagtgtgg tcgggtaaaa gtacggagca aaaggaaacc   17640
gctttaaagg ttgcgagctc atacgctgat tcgcgttggg ctgcacgtat tagcgcggcg   17700
ccacttaaat ccgaccaagg gttaagctta cccgcaaacg gcctgtacag cccacacggt   17760
gccgctgtgt cggggatacc tgttaagtgg aagcaagcgg ttatgaaata cgcattgcaa   17820
tcatttagcg gtgacctatg gaaaacagcg acgcaagctg atgtatcggg taaggttaaa   17880
agtgagcgcg taactgtagg cccaattaca acaaaaaccg agtttgcagc caccacgggc   17940
gcggctgtgt tgttcaaacg ttacccgaaa gcggacgcgc ttgtaaaagc tgcgtttatg   18000
tctaaaggct ctggtgggag agttatccga tgagcgatga tgcttttttac aacaccataa   18060 tcgaaaaggt tgtcccaatt attgagcgat ttggtacatc ttacaaggtg cgttctaagg   18120
gtgtgtacga ccctgacaca atggaaacaa gtgaaccaac tgagcgcact gttaagggtg   18180
ttcgcgctaa cggatttaca gcgtcggagc ttggttcaga tgttggtggt atgaaccgag   18240
gtggtgcttt cattattggg cacaactcct tgttaattga accttccgca acattcttc   18300 caacggatga ggtggaagtt gacgggcagt ggcaaagctg caaccgtaca gaaaaggtac   18360
agccgggcaa cattgtcgtg ctgtatgtgg tcactatcgg tggctgattt tgcatctgta   18420
attgagaagt tcggtaagaa ctcgctcaaa gcaattgaag aagtaaagcg gggtgctatt   18480
```

```
atagacctcg ctacttcaat tgtgatgcag acccctgttg ataaaggtta cttggctaac   18540
aactggtttc taacgttgga taaggaaacc ttcaaaacaa gtgacaaacc agatccgtct   18600
aaaatggagg tgcttgaccg cattagacgt tctgcaaaag ccatcaacta taaacatgtc   18660
gtttactttg ccaacaactt gccgtattct gtacctattg agtacgagtc ccactctatg   18720
aaagccccga gtggtatggt tcgcgtgaat actgcgcgtt gggattcaat tgttgaggct   18780
aacattagac gggttacgaa atgatttatg atgacgttga acaggctgta attaaagccg   18840
taaaacccca catcccatcg ggtgtgaacg ttagttggcc caactccgag ctgaccacaa   18900
agggtgaacg ttggttggat attgacaacc tatttgttga cgaccgcgtt atcactacag   18960
gtgacaaagg tgaaaacgaa attgcggta ttctgcaaat ccttgttaag attaaaccca   19020
acataggtgg caaatccgcc ctgtcccttg caactcgtct tgcaaagcag ttcaaagcgg   19080
gtaagagctt tacacataat caggctcatg ttatatttag gggtgcaacg cccggaccgg   19140
catttacgtc cggtgagtat tacacagtgc ctttatctgt taattactac tcaagatatt   19200
ctcgtacttt aggagattaa catggctgat ggaagtcgtc atacccttta tatggttgaa   19260
gagggtacaa ccaaagataa acacggtgtc acacctaaca cccccgctat ggcgactgtt   19320
cgtaatacgg gtgtaacgtt aggtcttgca aaagactcac tgcaatctga agagattcgc   19380
ggtgaccgtc aaattgcaga tttccgcttg ggtgcaaacc aagttggcgg tgacatcaac   19440
tttgaaatga gccacctgac ttttgatggt cttattcttg gtgctctaca agctgcggac   19500
tgggttgata ctaaccctgt taacgcaaag cagaagcaag ccaaagcggg tacaacccgt   19560
cgctcgttta caatgatgcg tcactttgca gatattgcgg acaaaccttt cttcctgttc   19620
aaaggtgttg aaattaactc catgaacatt agctttagtg cgaacgcaat ggtaacaggt   19680
acgttctccg tactcggtaa gtcacaagtg ttggggcta ctgcaccaac tggtgcaaca   19740
taccctgctg tgactacttc acgtgcaatg gatgcgttta caggtgcaat ccaagaaggt   19800
ggagagaaca tagctgtggt tactgaagct agtcttacaa ttgaaaacgg tttgaaccct   19860
cgctttgttg taggtagcaa agacggtatt taccctgaga atggtcgttc aaacgtaaca   19920
ggttcaatca ctgcgtactt cgaaaacgca gcattggttg aaaagttcat taacgagact   19980
ccaagctcac ttatgttgga agctgcggat actgcgggta acaaatacca attcttaatg   20040
ccgcgtatcg tttacactgg cggtcaacca gacgtagcgg gtgaaggttc tatttgtgtta   20100 acaatgcctt tccaagctat cctggatcca actgaacaaa caaacattaa agtaactcgc   20160
atcaacgcgt aaggataaca agatgaaact ggcagattta tttacccgtc aaactgctaa   20220
cgaaactcgt aacatgccat tggaattgcc ggatggttct gtgtcaactg aattccacct   20280 agaagttta agcacggagt cggatgcgtt ccgtcgtgct gaaactaaag caaaacgtcg   20340
cgcggttgaa gctgctgcta ttaaagacga agacgcaagc gcggacttcc aagcagaagt   20400
tgaaattgaa atgctcgctg cgatggttgt gggttggaac ttggatgaag agtttacgct   20460
tgaaggtgtt aaggaactgt tacgtgagag taacggtaac aaagaacgtc tgtcacgttt   20520
cactgctacc cgttcgcatt ggtttgaggt aaagcaaaag agctcctcaa ctggctcgaa   20580
gcagaagtaa aacttgaaaa gcgtccggag gggtctaaac agtccctccg cgacagctta   20640
ctacaggttc aaaaacaaac agggtttaca ccgccggaac ttcgagacct accagaaaga   20700
ccacctgaaa tggactacat ctggaaatgg tatcaacagt tgaaaggccc tcaaccactt   20760
agtaacactg aaattttaag ttgggcatgt ctttacggaa ttgaacctac accccgcgag   20820
```

```
gttgagcttt taagggacat ggacgacaca ctttggagag tcctaaacaa tggctgatgt    20880
agctcgcctc cagattaaaa tcgacagttt gtctgcagaa attgcagcac ttcgtcttga    20940
caaagtaact ggtgcgtccc gcaagaccca aagcgcaacc gcaggcttaa cgaaagtctt    21000
tgcgggcgca actgtggtca ctgctgcctt tgctgctgct gtcaaagcct tatctgttgt    21060
tgctgacgta agtaaacgtt ccaagatatg gaagcgcgt cttgtgacag ctacaggttc     21120
aatggaaggt gctgcgattg ctatggaggc aatcaaagac cttgctgtcg aaacaccttta   21180 tgatattgaa caggttacaa acggttttat ccgtcttgct aacttgggtt taagcccatc    21240
tgagcgtgct ctgcgaagct acggtaacac agcatctgcg actggtaagt ccctgaacca    21300
gttagttgag gcagttgctg acgccgctac gtttgagttt gagcgtctaa aagagtttgg    21360
tatcaaagca aaccaaatgg gcgaccgtgt gtcgttcacc ttccgtggcg taaccacaac    21420
ggttgagaag tcctctaaag ctgttaccga ttacctgact gcacttggtg agaatgagtt    21480
cgcaggcgaa atggaacgtc gtatgcaaac gctcggcggt gctgtttcca acatgcaaga    21540
ccagttcatc atggcggttg acaacattgg taaagcgggt cttgctgacc ttatggaaga    21600
cggtttccgc cgcgctaccg atgcgcttga gctgtttaac gcttcgatgg aatccggtga    21660
aatgggtgca cgcttggagt tagaagcatc ccgttggaac ttccttgctg aagaagcaaa    21720
cgcggcaatg gactggatga cgcaaatgtg gaacgaggtt ccgcaggagt ggaaagaagc    21780
gggggctaac gcgctacagt ttattataga catgtggacg tacctaccgg aaaacattgc    21840
atacgtgcac aaacgtatca ttattgagtt ccagtacctt gttgacgtaa ttcaacgtta    21900
cactagtaac attggtgagc gttgggagaa tacgtttgac cacattgtcg cgcgttccaa    21960
agtgtatgcg gttgcaattg gcaacgcatt agacccgttc agcgatgggt tcgatatgga    22020
gtctgcgctg aaacgtgtgg acgacttctt cgagggtgaa gctaaacgtt tagctgttaa    22080
ctatgacgac ctaaacgctg ctcgtaacac tgcattggaa ggtatcaaaa ccgagcgtgc    22140
tgttgcaatt gattcgtacg aagcgcagag tgctgcggtt aagcgtttgc gcagcagta    22200 ccttaaagac cgcgaggctc gccgagctac tgcgggcgac cgtttagcac agtttggaca    22260
agatgaaagc tctggtccga cacttgcaca acaacgtgaa gcggaaaagc aagctaaaat    22320
tcgtgagaaa gagtttgagc gtttgcagga gtatttacgc acggaagaag aaactattct    22380
tcatagttac aacaaccgta tgcgtatcat ccttgagaac acgcaagcgg gtagtgatgc    22440
gcgttctaac ttgcagaagc agttaaacga gaagttccgc gaagaggttc ttgacgagga    22500
tattcgtaac gacgattacg accgccgcat tgagaagctt gttgaatact acgaacgtcg    22560
tcgtaaccta attcttgaga cacgcagtt aactgaagag cagcgtacag agcttgagct    22620
tgagctaact aagcaacgta acgaccagat tgctgctttg gaaatggaga aaaaccagtt    22680
catttcgcaa acagcaatgt caatgtcaaa tgacttgcta accattgcga agggtttgc    22740 gggggagcaa agtggtatct accgcgtcat gtttgcagct tctaaggcgt tcgccattgc    22800
ggactctatt atgaagattc aacagggtat tgcgaacgct gcgtcattac cttggcctgc    22860
gaacttgggt gctattgcgt caactgttgc tgcaactgcg aacattgtta gtacaatcca    22920
aagtgtccag atgcaaggtg gttcgtacgc aggcgcgtac gataagggtg gtcacatccc    22980
tgccggtcag tttggtattg ttggtgagca tggtatggag ttcgtaaaag gcccagctaa    23040
cgtcaccggc cgcgaagata cccgtaagct actggagcgt gctgcacgtg gtggtgattc    23100
aggacaaggt ggtgcacaac aagccttgca aagtccaaca acattcgta ttattaactc     23160 cgtagaccct gctctaatga ctgagtacat gggttctgca gaaggtgaaa aagttattat    23220
```

```
gaatgttgta agacgaaatg gtcgcacaat taagcaaatg gtggcgtaat ggcatatcaa   23280
actggtacgg caaacgggta caaagacttc cttgggaaac ttcgtacctt tgcactggct   23340
aacgggtgga cgcagaagcg ttcgctcacc cccgcaaatg cggaacacga gctgattatg   23400
caatctgttg gtgatacagg taacgacgcg attacccttg cgtggaaaac ttacacaaac   23460
acgcaggcag atatttgcaa tcttttgtgt aaagcttcaa acacctatgt cgacatcccg   23520
tttgaaactc tcacaaatgc aaacgcggag acggttgtgt atctttggga cggtacgatt   23580
gactatcata taatggtgaa caaggaacgt atcatgttcg tgtgtatggt gtcgggaacc   23640
gcgcaatatt actatggcgg gaatatgcga acgtatacat cacgtggtca ctggcctaac   23700
ccactctgct gttttggtgt tggtacggat agggatggtc gttggtctag tactggtgac   23760
gactactcgg gttggcagta cgttcgagga actaagcctg ttcctgtgta cgatgagaaa   23820
aaggcgtggg ttaagatgtc ctacattcat ccgttcatgg ggcatcctca cagactctcg   23880
aactgggcac cctaccagaa cggggacagg gcgttgttgc aggccattat taagatagat   23940
ggtcatcaag tggttggtga gctgattggt gtttacggaa ctgggggtct aggtcttgca   24000
aacgggcagg agttaaccca ctcgaacggt aataagtatt tagttgttca gaacgtttat   24060
cgtgcgggtg gcggtgacta cttaattatg gagaaattgt aatggcatac gctacacaaa   24120
attatggatc tgcccgtact gacttgatac aagctttaag gactcagttt gaagccgcgg   24180
gatatactat cgcggggcat gaggggggaaa gcctttgtgt taagttaggg gacgacccttt   24240 tcgtggagta taattgtaag aatacccgat acgtaagtcg gggcactgga gaatacgcgg   24300
attcactaag ttggcgtatg ggtacttccc acaacggcgc tcaagtggct ggaaacacgt   24360
cgcccctaga gagtcacggt attgctagtc ggggatggag tggtcctaag caacattgcc   24420
cgttgccggg caagcttcac ttctgcaaga cctccgtatc cggtaaattg gactacgcat   24480
tttgtcttga aaccccaca gacagcaagg gctctactta cgttggagcg gagctggatt   24540
gtgttgaccc acaattcggg gcgtataaac atttctactt ggcaggtcag tatgcggttc   24600
ctggtgggtc cgatgaggct aaccctggac cgttccacca taccagtgac catacggggc   24660
ctgggtacat acgtcggcag aacgcagacg gtactttcca ctcgtatgag cgggcaggct   24720
acggcattaa tagcacggtg gatttcaaca caatcaatag cttccttccg gttgggccac   24780
atgggttcta cgatggtatc tacgatggcc tgtacttcga tccgtcactg actacagttc   24840
tactcccggc gatttggggg tgtgttcaac caaagagcac gtcttcggat ggtcgttttg   24900
gcgcgccccc gaagggtgag ttttcccagt tcaaggttgg gtctatgaag tatgttggca   24960
ttggtgggga gctagtacta gatggcaaga aatataggtt gttcctcga attgggaagg   25020 gtggcactaa caccgccgct atagctatac gtgagagtta actatggcag tagttcatat   25080
atttggtaag ggtgtatcgc acacccttac ccctgagcct ccattgccaa ccgcaacccc   25140
tgttgttgcg gggggtaact cagtcctggc tgtgggcgca tcggcaaaga ataagtgggc   25200
aacatcaaag gggttcgcaa cactgggctt tgttgttacc gggccttggc aatgcctaaa   25260
gaactctgtg ttttttgacac ctacacgtgt tgaccttggg gtgagcgctg acgttgcggt   25320
gcgtgagttt gacatgtggc acacgttctt acaacccctta acaattagta acattgttca   25380
agttggtaca cgtggaatga cgctaacacg tgagggtgcg ggcacgaaag atcttattcc   25440
tgcattgggg cgtgccaagt acacactcaa cgttggggttg cagaccgaaa caattattga   25500
cgcaacatac acatggaaga cctcaccgtc cgtaaagaat gctcaaattc gaattactgg   25560
```

```
ttcgcgtgta gtcccgtggc cttacttgcc aaagggtgac tttgttgaaa cgcgtgaatg    25620
gttaaccgac gttattcgca cacgtaaaaa ggaacagcgt ttgtctttac gtcgcggacc    25680
tcgaaaaaca gtttcgttag cgtaccaaat tagcgaagcg gacctcagca atatgtggtc    25740
acactctcga gtatgggtta accagacata tgctgtgcca gattggacta agttcttgcg    25800
cgttggttca attggtatgg gcgtaactga actttcgttt gacgcggtgt cacttgggtt    25860
ggtagcttcg ggatttgcgt ttatttatga caacaacgaa aaatacgagg ttcgcccggt    25920
caaagctgtg accacaagta aggttgagtt tgttgaccct atttcgcaag cttacaacga    25980
cgcgactatt gttgttattg agttgcagaa acacgatcag ccgttgcagc ttacccgtac    26040
cgcctacggg gttgcaaatg ctgacgtaac gtgggaagtg ctggacgata cacttaacgc    26100
tagtaacccg ttcccgttgt acagtgggat acctgttgta accgaccccg tcgttatggg    26160
tggtactact caaagtgagc aatttggctt cgacttagac cgcattgata acaaggttgg    26220
tttgtacact gattttcagg agtatggttg ggattcccgt acacgcgctc agttacggtg    26280
gtcttgcgac actagagctg agtttgagcg tgtgcgcaac tttcttgact tttgtcgcgg    26340
taagcagggt gaattttggg ttccaagttg gaatactgac tttattcttg cgcgtgacat    26400
tgttagttcg gacggtgcat tgcaaaccgt gagaactgct gcgtcgctgt tcttcgaacc    26460
attccatgta atgatagagt acgtggacgg gacgttaggg tatacaaagg tgacaagtgc    26520
ttctcgcggt aacgactttg acacattgaa ggtttcgcct gtgctagggg acaagccgat    26580
gtcagaggtc aagcgcatta tgcgacttaa ccgtatgcga tttgatacgg ataggtttga    26640
gttccagcgt aaatctacag gtgtaattga cattgctgca cctattgttt cagttccgga    26700
ggtggtatga gtaacccaga cactagttat tccgcgggtg taccagtaga aatgtacatg    26760
tttgagcagg gtacttccgc tcgctatttt acgccccacg ctaaacctgt ttctcgtgga    26820
aacttaatac acgaacctaa gaacattcag cgtgacgatg tggaaatgag tgacgactca    26880
tttaagggta cgttaacctt aacgttaccc cgaaacgacg cactagctgt tgagttaatt    26940
ggcgcgtcgc ttgaaattcc aatggttgta actttgttcc gcgggcagtt agatggttcc    27000
gcagcaaagg aagtgtccgt ttattggaaa gggagggtag tgacaaccaa ggcgcaagat    27060
aatgtggtca aagtcgactg cgaatctgtg tttacagccc tgaagcgtgc ggggctacgt    27120
gcccgctacg agaaaacatg tcgtcatgag gtgttcgacg gaggttgcaa gcttagtgaa    27180
gcaacttacc gcaaagttgc aaccattggg tcaattaacg taatggacat cacgcttact    27240
ggtgaagctg ctgcggttgg ttattacact gcaggcatga ttattttccc tgacggttcc    27300
acccgattga ttaccaagca tgaatccgcg ggtaaaatta caatttcgcg tccgcatccg    27360
ggcgcggaag agggtcagcg cgttacatta cttccaggct gcgaccactc gcaagcaacc    27420
tgtaagacta agttcaacaa ctttatcaac tacgggggt ggccttacat tccaattaag    27480
aacccgtttg gtggtagttc atttacatag gtgataacat gtggtatgcg ttagcggtcg    27540
tagttgccgc gctaattatc ggtcaggcaa tggctccccg aacccaagcg gtgaaacctt    27600
cggggttaga tgagttccaa gcacctaccg cagaggttgg acgtgaaatc cctgttgcgt    27660
ttggaacagt tgacgttcgt ggtccgaatg tggtatggta tggggatcta cgatcaaccc    27720
ctatccggaa gtaatatgat agtcaaatta gagcatgtcc gtcaggtgca cttttgctca    27780
cgtggtgttc gcgcatttttg cgaacgccac aacctagact ggaataagtt cattacagag    27840
ggtttgcccg aggaagagat tcttgctacg ggtgaccaca tggctcgcga agttgtggag    27900
gctgcatggg cggcaagaaa aaacaaacag taggacaccg ctattattta gggtttcaca    27960
```

```
tggcagtatg ccatggtccg gttgatgagg ttacagacct atttgcggac gaacgccact   28020
tgggcgaggg tagaacaagc tccggtgaaa ttacagttga taaagcgaac ttatttggtg   28080
gcgacgaccg tgaaggtggt atctcaggta agttcgattt gttgtttggg gaaccaacac   28140
aaccccgcaa cacttacctt caggagcagt tgggtactga cattcctgcg tggcgtggcg   28200
tgctaaccat tgttgcgaag cagatttata ctggtacaac gtcttacctg aaaccaattt   28260
accctcgcgt gcgacgcatt atgaagaaga cggacggttc cgctcaatgg gagccaaacc   28320
ttgcgcgtat tggggacgat atgaaccccg ctcacattgt gcgcgagtgt tgacagaca   28380 cagcttgggg tatgggttat cctgcaagct caattgacga tgttgagttt aaaaaggtta   28440
caactactct caaaaacgag aacttcggtt tatccttact atgggataag cagaaggaga   28500
ttggcgactt tatccgtgta attatggatc acgttggtgc tgtactatac gttgaccgca   28560
caacgggtaa attcgtaatg aagttactac gcgcagatta tacggttgca acattccaa   28620 accttgggga agacgacatt gttgagatta gcgactttgt tcgccctaac gttggggaac   28680
taactagtca agtgacggtt aagttttaca accgtgcaga agcacgtcca gactccatta   28740
cggtacagga tattgcactg tcacgccaac agggttctcc tacaagtatt acgaagcagt   28800
tccaaggtat taatacccct gagttagcga acacagttgc agcgcgggag ctgcacgcag   28860
taacaacacc gctaattggt tgtaaaatta agtgtaaccg aatcaaagcc gcctctttaa   28920
cagttggttc accgtttgtg ctaacgtggc cggactatgg tatccaaagt gtggtcatgc   28980
gcgtatccaa catcagttac ggtacaacca cagacgggca aatcacaatt gactgtatgc   29040
aggacgtgtt cggcattggg caagcgttgt tcgttacacc gcctgacaca gaatggaaac   29100
cacctgtaac agagccagcg ccagcaacta gcttctacat cgacagcacc ccataccgtg   29160
aaattattca gcgtttgggt actaacttca ataacactaa cctatcgggg cgtgaatatg   29220
tcatgggttg tgttgcacga cctgcgtcgg actctattaa ctgtgagttg tgggtagacc   29280
aaggtggcta tcaattagca gatacgttgg actttgttcc gcacggtaaa actgcaacag   29340
cgttagaaca gtcaacaact aacttccaaa ttgttggcac agttgacgcg gacttggttg   29400
cggttggcac tgcgattgca gttgacaagg aatacatgaa gttaaccgcg tttaacccaa   29460
gtacaggtca atgtactgtc gagcgcggtg ttatggacac ggttcctgca agccacgcag   29520
cagacacaac agtttacttc tttgacgact ttgctgaaat gtacgattca gctcaggagc   29580
gtggtgtagc gttgaaatat aagttactac cctcaacact gcaaggtcgt ttggagttga   29640
gcaaagatac tgagaagtcg ttcaccctg tacgtcgttg ggataccccg taccctccgg   29700
gcaacgttaa aattaacggc atgcactatc caaacacgtt cagcgggaac ctcgcaataa   29760
cgtggtcaca ccgtgaccgt attcagcaac aagacaagct ttacggattt actgctggca   29820
atattggtcc tgaaaacggc acaacttaca cggttcgtat ttacgacaac acaactggaa   29880
ccctcattcg tcaggagact ggtatcaccg gaacgagttt cacgcttaac aaagcggatg   29940
aagtggggat cttgctacct gaattttatc gtgtagaggt tgaatcaatt cgagacaaca   30000
ttaagagctt ccagttccaa cgtgtcataa caagacgtac ggacagggag gttccaccaa   30060
caagtagaac atacactgtt actgttggt ctaatgcac aatagttggc tatcatgaaa   30120
ttggaattgg ctcggtttct ccaaacgttt gggaaccaag ttcggctggc ggtgtgagaa   30180
ggttgggtat caataacaac gttttcggtg ttaccaacca agatccaaac tatgccttgt   30240
gggatggtaa cgcccaacaa gtgagggtaa catgtgagca aggcggtctt gattccgtat   30300
```

```
ttggtttgca atcatgggag gctggtaaag gtacttacga tcggcaccaa tcaggtaaca    30360
cctctgcaca gtggaaaacc ttcttggagg gtcaagttgg caaccaagtt accattgtgg    30420
ttgccaccgc ataactgtgc tttacgcgca ttcaaaaggg ggtacacact gtgttacccc    30480
ctagccaatg caattgtacc agtaaataaa aagcggcctg tatgggccgc ttatgcgttt    30540
atgcgtatgg gggttcccaa tagccataag cccagtaacc cataacgtat ccgcagttct    30600
tgcactcctt acgcacctcg caaggtgtcc aatccaagcg gtctgtcaca acctcgatat    30660
gatccatcca atgccagcta ttgcactgag tgcagcgaag tggctcaccg tccattgcaa    30720
agtaaccgca ccaaacagca taacgccagc gccaccagtt aatgcggtga gccacacgct    30780
gtttcagcgt cattttgatt ggaaaattta cttgtgttgg gtgcatgtgt taactccgaa    30840
aacaactagc aaaacaaagt ccatttgacg ctgtgttaca acctcagccc ttgcgcgaat    30900
accaacaaca cccgagcaat atatcttact gaccacatgt gcagtaaatg gcacgccgaa    30960
caaggttccg gtaacgtgtc cgtcctccaa gtccgtccat gtaccagtaa cctcgaggtg    31020
tgtttcaatt gccccctggca cttgttctat gatgccaagg aaagaacgat attcttctct    31080
tactgttagc tcgcgcgaac ctgttttaac ttctttcccg tctaagtaca acttaattcc    31140
cgtttgcatt tcgtgcaccc tctctcattg caaaatcttt aacgaaagct ttctcaagcg    31200
acttggtatt ggtacgcgat gccataccccc acacaaggaa gaagtcaata agaaccatga    31260
taccaaggaa cccaagcgtg agcgtgtaca aaatgttgaa cacagtaacc cctttgacgt    31320
aataacggtg tgcaccagtt acgccgagca ataggaacaa caggatgcaa actccagacg    31380
atttagcgtt agtttgcgcg atagtggtgt taatgtatgg tgtggtcatt attctaattc    31440
ctctttcata gcttcaatga acattcgagt cgcttctgga atgcaagata cgcgtgttgt    31500
gcgcttaatt gttttgcggt tttgcttgcg acgctgtgca cgtcgcgggt caagcgtttc    31560
acggtcacgc gcttcgagtt tagctctcgc ttccttgttg ctgtggtact tagcttccgc    31620
aagtgcaccg gctgcgcaat gtatttcgtt aaactcggtt aaaccaataa ttcgcttggt    31680
ctccaagtac acgttgaaga tggttggata tgcggtgtaa gtggttaacg cttcgcggtc    31740
accaaccatc cacttgaagt tgtacatgtt accacttagg aacttagcga tacacacgta    31800
tgttccgcgg tggtttggtg gctcgtcacc tgtgcgggcg tacacgcgaa catgttccca    31860
cttttcgtca cctgtgctgt tgcggcgtgg gtgcaacccc atttgtttca ttacgtcaat    31920
aaattgtgaa ataaccattt tgtgaacctt atgcaaaaac ccctgttaca gaactaacta    31980 taacagggggt tacgttttta aactagacta ttcagcgcta gggtgtccaa tatcttttag    32040
gatacggtta gcttcgttaa tgtaccaatc catatccaaa tcctcaggca gctcatccaa    32100
cattgtcatc attggttttg caccttcggt ctttggaact ttgctaccct tttcagcttg    32160
cagaataaca tacttggact tctctggtgc tttcgcgtag taccaacgaa tcgcaccacc    32220
aaggtagtcg tagtccacag ggttccactt actagcttca aacgcttggt ctaagcgaca    32280
cgcttccttg tccggttttt cactagcact gtgaacccat aacgttccca catacgggat    32340
gtaaccgcac ttgcgaacat gctcttccat ttggtcttta gttgggtttt caaagtccgt    32400
tctgtacata caccaaacag aaccgccaga aaccttacgc actgagctaa acataaacgg    32460
gtctttacac gccgtaatag tttgctcaat aggtgtaccg tgtgccacaa acgctttttac   32520 tgcctcggca cagatcggtg tggttgggtt cttggatagc ccaggcttcg cataaatacc    32580
cttcgctttc acgtcggtct tcatttcacc tgttttcttg tcctcgtaag gcatcttaac    32640
cgcgaaatag ttgtttacgt cttttactaca aagtgcttga tagtaagttg cttccaactc    32700
```

```
gaacgctgtt acacgctgcc accattccaa aatctgctcg cgtagctcaa acttagactt  32760
gtgacacttg attacaatac catccgtgtt cgcagacaca acctgaatcc cgttaagctc  32820
gaacgtctca attagcagta atagcgataa ctgacccgtc agcgttacgt gaataagcaa  32880
gtccggtgaa tagaacagtg agtattgtga acccaattta ccaaatgtac cgttgataac  32940
gatcttaagt gattgtgcgg ttttgctgtc cccattatgt ttagcttcca gacgcgtttc  33000
aacaatgtta tcaaacacag ctaggaacgg gcgtcccaag tgctgcgggt aatagttgtt  33060
gttcaacata atgcgcgggt agtaggacgc tacatcgtgg tcacttaatt ggtagttttc  33120
atcgctaatg tgggtagctt tcttctcggt actgtgcaga ccaccgatac caagcttgta  33180
cgacatttca ccaatggtta ctttcaaccc tttaagctgt gcaggggttt caataccacc  33240
tttgtaactg accacatata ggcagttctt aactacctcc agtgtctgtt tcattagcgg  33300
tgtttggaac tgcaagaacg ccggtgcatt gtagcggtaa accgttcccg gctcaatggt  33360
tggtttctgc gggcgtttac ccgttaagcg ttccagctcg tgtgcaatta cagcttcagc  33420
aatctgtgca tcggacttac tacgcaagtc cacaccgtat tgctcgctca tttcttcacg  33480
caacttcatc tcgtcctgaa tcttgctcat tacggttgca gttgcgtcca agtcgtttgc  33540
ccagtagtag cgcgttacag cgatttgatc aggggttaac tcaacgtcgt gttcgtaagg  33600
caagtcctgc atacgcttac caccagaacg accgttgtag attttcaagc taccaaagtt  33660
tggagcaact tccatgatat caatatggtt cgcttcaatt ttctttaggc gcaacttgcg  33720
caacacttgc cagccacggt agttttccat gatcatcatg ttggttgcgg ctttcatctg  33780
tgcacacgat ttacccgcga ttgccatagt agcaagggtc atatcgaatt ccattgagtt  33840
aaacccaaca aaatgcatat tgcgcacaaa ccagtccagc attggtagcg gtaagttcca  33900
atcgctgtca ccgtagtcgg tagcagtctt ttcccaatag ataattttgc ccgtgttttc  33960
gtcacggaaa ccaatcaaac accagttgat gtaagactca atatcgaacg tgaacaagtg  34020
cttttgttgc caagcgtcaa ttacgtcatc ctcagacata attgagatac ccgtcatgtt  34080
tattgcgtct tcgtaatatg gcaagtgtga gctgcacttc caagttgcag gaggaaggtt  34140
gaaaatctct tcctctttct ttttcttaaa ggttggcatg tcttgccaga acaaacctag  34200
cgcatcagca cgcatagact aataccccccg cttctccgc ttgcttacac atgtcagctg  34260
tacccgtacc gccaggaaac gctaacagta aatccggttg tgtaaatttc aacatccaac  34320
cgttacgaat gttacctgcg ttgttaccgt agaagtccca agctgcgttc attgaaataa  34380
caggatgtcc gtttgtgatt gcccagttct tagcgtgcca gtcaacccct gttgcgtcac  34440
cctgcacaat aacaaattcg tcatcaaaga acggtaagca ttcttcaagc ttgcgctcaa  34500
catacgcacg gtcgttaaac ttacgccccc cagttacaag aataacttta ggtttcatta  34560
tagacgccct tctaaccaac gtaacccaat aataacaccg cggatatttt caccaaccca  34620
cgggcacggt ttagggtact gagttaaatc tagttttgta gcaaccccgt ccaatttacg  34680
aagcatgttg cacacaaatg tagagcggtt tttaataaac tcgcaatcaa caatagcacc  34740
ctcttcgtca ccgtccaagt gggtcatcat cttttccttct tccataagca cgcgaccgat  34800
cttatccgta aacggggcaa tgtggtcaag cgagtcataa aagctttgcg ggatgtcaac  34860
cataccttcc attggggctg taagcacctt agtcatgtca ggccacttct cgtcaattag  34920
caaggtgcgc aaccaacggt caccgctata gtgcaacgtc aaggattggt cgtccatttg  34980
aaagcgttca ggtgcttctt taaggcgaag gatttcctta actgcgtcgc gtggaatgac  35040
```

```
cacactgcac gggaatggtg aaccgagcca atattccgct gcaatgacgt tgttagttgc   35100
gaacgcactg ctaccactaa atagcacccc gttagaccaa gggcgcgaag catcgtctgc   35160
gattagcggt tctagtgttt tgagcgcttg taacaactgg tcgccgttaa tgtcaacaaa   35220
agcaccgctc ggttgtgggt gtggtggttc aatatctacg cactggatat acgaacggaa   35280
cttgccgctt ttaactgaaa gtttgccagc gggcgtcata cctagtacaa cagtatcttc   35340
acactgttgc aaagctttca ccaagggtgt agcctttggg atacaatcaa catcaaagtc   35400
gattggtgca cttaacgaga tacgaccgtt gtaccccgtt gcgcgttggt tttcaatctt   35460
aaagtgggat agggcgggta ggaaatcttt cttacttacc gaacccatta cgaatttcag   35520
ttctttaagc atttacgtcc acctttacaa agcgaccgta tgttgaacgc tttactttct   35580
tttcaaacat taactgacct agtgcaaact caacgggtac ggttgccact ttaagttggt   35640
tacacagctt gcgaacagtt aaaccctcag cattttcttt atcagcaagt agctttagga   35700
tgttttcttg taattgtgta tatacgctat caaacattaa aatagtcctt gtatcatatc   35760
tgctttggtg ttacgcttgt gtttgttgac aatttcgtta attttcatgt aagcgaaaat   35820
gttgtacacc gcacgcgatt cgtaaattgt cgctaaacgc tcagcgtcaa agccttgcga   35880
ctgtaacagg ttgtaaaggt gttcgcgctc aattggcgac atgttttcaa tgtgttgtcc   35940
caactggtgg cgcgacggtg acttctcaga tactgaaagg ttaattgcac ctttacgctc   36000
atccggtaga acaataccac caaaagatgc ggactggatc caggaagacg agtcacagct   36060
ataccaaggg taacgctcca tcaacggaac tgcggtgata ccaaatccat gcaccttaat   36120
gcgcgggttg ccacttgggt cggtgaggta gttatcccaa atgtggtcaa gccattgcat   36180
caacgcctgt gttgacgcgc caaccatacc accgagtgtg atgtaatcgt agttctttac   36240
ataccactct aaataacgct catcttcgtt tgcgtggaaa cagggtaacg gtcgcacacc   36300
taaacgttcc attgccattt ggttttcaaa cgtttcttgt gggtcaccga taccatcgag   36360
cacggacgcc attaggtttc catcttctac gcgaataata tcactgttgc gtaatatata   36420
gtccacatag tcttccacct ttagtttaac gccgagtgtg tacgcagaga acgcaccact   36480
atcgaggaag attttttgcgt cgttttcacg catgttgtta acatagcttt gcttgccaac   36540
gtagtgccaa gattcaagga tgttgtgctg tttagcatcc atcataattt ggcattcttg   36600
ctcattgagc ttaggccaac ggtttcctcc cggcatatag ctgttcgtgt aaaccgcagc   36660
taaatagact tgtaatggtt gggacatgtt actcactcat aaataaccag taagggaaag   36720
aatgttgtga ttgtggtgtg ctagtgacca caagtttgtc gcgtggtggt ttggttacgc   36780
gtgcgtgcaa cttgtccagc gcggcaacgt ttgggtcttt agggaagtca atcgcgtttt   36840
gacgctttag ttcttcgtac cacattggac tgacgttaat aacacagcta tctggtgtgt   36900
caataatagc gtccattgct tggttatgac tggtgacacc gtcggggtgt acaaccacgt   36960
ttcgacccat gtataaagga tgtgtttcca tattttactc cggtaataaa aaaggcgtgc   37020
aagtataata acccacacgc cccacctatg ctagactaac cgtaaaactt cttgtgaaga   37080
tacgcaaagg ttactgaacc aagcgcaccc cctagcgcaa ttggaaagaa cgcttgccaa   37140
ccctcagtga caatccccgt tacaccaatt accatggata agtctatgcc tatactcgtc   37200
agaaacatcg ctttgtagtt gagggaaaca atattccttg tttgcaccac acgcaacccc   37260
actgacagga atgtggcgca aaagagaact aaatacgaaa ccattagagc gccttgttaa   37320
tatttcccaa agccatgaac tcggcacgtg tttcaggttc agttttgatc gcaccacgta   37380
gtgcggttgt gacagtatgg tgcccctgct gacaaactcc gcgcgactcc atgcacatat   37440
```

```
gtcgggcacg aatcttaact ccaacaccaa tcgggtcaag atgctcaacg agggcgtccg    37500
caatttgcgt cgtaaggcgt tcttgaactt gtaagcggcg agcatacata tcaaccaagc    37560
gagacagttt actaagaccc acaatttttcc cgttaggaat atatgccact gttgcgacac   37620
caatgatatc agccatatga tgctcacatt tactgtaaaa agggatatcc acaacagcga    37680
ccatagaatc agcaccttcg gcgccatctt caaaagtctt aaggatagat ccagcatcca    37740
taccgtaacc gccaaaccac ttagcaaaag ctttagcaac gcgctttgga gtttcttgga    37800
taccttcacg gagttcgcag tttgcatgat caatgtcacc caccgtttca gggttttcaa    37860
ttaggcgtag ctgagcttca acaagttttt ccatttcgcc cattacgcga ccgttatctt    37920
tattcatttt aaatacctat accaagggtt tcaaataacc aaaccgctga cggttcacca    37980
agttttgcaa gaattgcggc caccatgacc gcataaagta aaccaattaa tccaaagaac    38040
actctaccga acatttgcga gtctcctcaa gtacaacctt tgttagctgc acaccagtgc    38100
cgaacagcaa cttaggacca atgtggtcaa ggaagtacgc tgcgatgttt ccgctgttg     38160 ggttgaaatc aacaaacaca aatgagtttt gcatgtcagc aatgtcctgg tcttggagaa    38220
taataccatg cgcttcttca gcaattgggc gcataatcgg atcgtccaac caagccataa    38280
acttgtgatc ccaatggtct tcaatccact cacaaagcag ttgcttaatt actgaaaagt    38340
caattacgcg accaacttca tccaagtgtg cagcttcaca gtggaagtga atgcggtaat    38400
tgtgaccgtg caagtggcga catttacctt cgtgacctac aacacggtga cccatgcaaa    38460
aatcgtggta gcgaatagct gtttgtttca ttagtggttt tcccatttca gataaccccc    38520
gttaataggg gaactttat acacgtaacg tccgtgcata ccattagcgt tgaatgttaa     38580
tgtaccgcta tttgggcatt caagcaagat gcgttgttgg tggtatggtc caccaacaca    38640
cacgagcccg ttattcgcaa tcagactcat aagtaattac ctcttccaaa ccgttaattt    38700
cgaaagctgt tttacgcatg aagcacggac cacactgacc acagtgttgc tcaccgtgtt    38760
tgtagcagct ccacgttaga tgaaggggtg cacccacttc gtgccctaat gctacaattt    38820
catgtttcat taggttgcca actggttgaa tcacttccag tttaaatccg tcgcgtactg    38880
cgaacggtaa cagcgcatta aagcggttga taaactcagg ttcgttatca gggtacgcac    38940
ctgcttcttc gaggttgtta cctagagcga tggtatcaaa gccgttagct tctgcaaatg    39000
cagttgcata cgataacatc acaaggttgc gagcaggaac ccattcgtgt gcaaactccg    39060
cacccgtttc accaccggca atcttctcgt ctttacgaag caaaggtgag tctttcgggt    39120
catacacgtg cattggaatt acatgcaacg gaacatccat gtattctgca actgcgtgaa    39180
ccgcttccac ttcgtgctgc tcagcgcggc aaccatacac aaagtgcaca agctctaccg    39240
agtaaccgtt tgctttcgct gcacacgctg cggtaacact gtccaggcca ccactgcata    39300
ccacaagtgc acgcttgcct gtgccgccgt acagcgactc tgtgtgcatg atgccaaagt    39360
ggttaaaaca tgcaaccgtg taaggtgcaa gcatttgcgg aactgcgttt tcgtaagtat    39420
cttccaagta cgctgctgag cttgcgaaaa acaccccgct ttccgttact gtgtaccaca    39480
ctggacggta gtttgccgct acatacatcg ctgtctcagc acggttgtta atagctaaga    39540
ttgcatagct acccttcagc gactgaatac cacgcttaaa ctcttcaaac acttgacgcc    39600
agtttgcatt gcgaggcatc atttttcatgc actcggggat tgcagcactg tcaatttgcg    39660
tttcaagttg gttggtacgc aactccacgt catttgcaat tgtgccgtta tgagctacaa    39720
cccaaccatt cgcacagtac ggttgttgat caaacttctc tttaatctca acgaactcag    39780
```

```
ttgttggttc tgcacggaag ttaccaacta cacgcgagtg acccaatgca atatctggaa    39840
cgcgaaggga ctcaacgtcg aacgggccaa cttcatgcac aatgtcgttc agcattgact    39900
tttcgtgggt gtgtacgaaa ccataaccgt cgcgaccgcg ctcggtacta cgctccataa    39960
ttgtggtcat agctgtttga cattggattg tttcgtagtt ggttttaggg ttaagaattg    40020
caccaaaaat agaacacatg attgtttact ccacgttaat taacttgtgt acttgtaagc    40080
atagggtgta accgtgttgc atacaagacg tcttaacagc ttctaagttc ttagcgttaa    40140
caacttcatc cttacagtcc attggttgta ggaagatctt aacgttatcg aattcagggt    40200
agcccatctt agctttaagg tcaagtacac gtgaaggtaa accgttggaa gggttaacat    40260
gacagtagtg aaggacgtac ttgtaagctg acacatacgc tgcaatatcg cggttgatgc    40320
gacccttcgg ggagcacatg ataaataggg atttaccaag gaacattgaa cacaggtgac    40380
gcatgttagg tgtgaggcct agcgtaccat tagtttcgat ttgcactttg taacccttac    40440
taatgagtaa actcactaaa gcgtacaact cttgtcgtaa aggctcacca ccactaatga    40500
ccacaagttt gttaggtgag gtatgcattc cctccacctt ggctgtgatt agctccgcgg    40560
acattaactt agctccgtcg gtgtactcgg tatcgcatcc aggacaacgc aagttgcacc    40620
cgcttaaacg aacgaacgtt gcaggttcac cggagaaaat accttcacct tggatggtgt    40680
gaaaaatggt gtgcaccaga acagctccgt ctttacggaa gtccggttta gatataggtt    40740
ggttattcat ttgaatcctt gttttgaact ggtaaggtta cagttagagg gattggtcgg    40800
tgttacagga ttcgaacctg tgacccccttg ctcccaaagc aagcgctcta ccaaactgag    40860
ctaaacaccg tattggacgc aaaacctaat tttgatagct accagtatac ccgcgatcta    40920 cacccccacaa gggggattgt actggatgat ttaaggactc ggataagtac cactatcaaa    40980
accaagtttt gctgacgatt aaagcgaggg atcacacctc gcaacatcgg ttaatcttaa    41040
agtgcgccga ctagcactac cggagaatta ttctgcgtct ttagctgcgt tagctgcttt    41100
agctgctttt tcagcggctg ctgcttcagc tttagctttc ttttcagctt ctttagctgc    41160
ttttgcttca gctgctttag cttctttttc cgctttagct gctgcacgct cttcagcttt    41220 acgcttttc tcagcttctt tttcagcttt agcagcttca cgttcagctt tcttagcagc    41280
gcgttcttct tcgcgtgctt tcttagccgc ttcttttttca gctttcttag cttctttagc    41340
agcttctttc tctgcttttt cagccatttg cttttcagac atgatgcgac cagttacacc    41400
gtggaattta cgccatgcag cgtactcaca acggacgtta cctgcgttaa gaccttcagc    41460
gtcagtaacc acaagtagat ctgcaaccgc taccggagcc tgtttcttag ctgacatttc    41520
gtccgcgata gcccatacgc gaccacatag tgtgtcgggg cgtggacgtg ttacgccgtt    41580
ttgagaaggc attttaggct tttcaacttt ttcttttctta gcagttgctt cgccttcagt    41640
agctgcgcca gctgcttcag tgcttgcttc aggttctgct tcagtaccga aaccagttga    41700
tgcgaaaagt ggaagtgcca aaagtgctag tttgttcatt gttctgtctc cgatagtgga    41760
ctaaatttaa aaagttacgt tttaccgctt tagggttccc attatacgga aaactcccta    41820
cagtgcaacc cctaaagcaa ataatttttaa cgtgttatca agataccaag cgtgactttt    41880
gccaagcacc taaagtagat gaagcagtgg tcttttttgat accaatagct tcccaatcgt    41940
tcatccattg cttacgtagt ttgaggacaa ccgatacatc tgttggttta cccgcagctt    42000
cccaagcttg gtcggcaagc tcaaaaatac gctctttttgc accgctttga cgctcgcctg    42060
tgccacttgt gctcggggta gcagcggcgc gtggctctgc tgcgggtagt ttacttggct    42120
tagttggtac gcggcccagc gcgccgtaca gtgccccgac gctacgctcg tctttgacgt    42180
```

```
cacgcgctag gtttaacagt aaaccaacca agaattcacg gtcgttacgg tcgcgttggt    42240
tgcaaatcgg agaccctgta gtgtggtcat aaatggtcgc caactcagcg ttgctaaaca    42300
cttccaaccc gtcgaacccc atgtcatcaa tgtgcgggtt gcttttaccg tcaaccagta    42360
ggtcggcaag gtactcagct tgttccattg tgtcagtggt tgcgactaac ttcatgctag    42420
ttgtatcgag tatgtaaagc attatttaag ctccaagtta aaaaacgttt ccatgtgttc    42480
aataagctca tggtgggcca ttcgatgctc cccattggga tatttcttac tatcgtatct    42540
aggcgtgtaa agagaaccgt cttcaacttc cacaacgtaa acacctctgc ggataaaagt    42600
acgaactggc ttaccaaggt cacacatacc acagcctttg tccttttcgg caaataaacc    42660
tcgaacacta acttgtggat tgtaaataca ttggatcttt ttaggtggta cacactcacc    42720
cgccgcttca cggtacataa tcattgcggt gaagttgata acgcttgcat ggtcgttatc    42780
cgctaatgct tttgcacgca tgtccattag gtcgccaatt gtgcaaatgt gttcgctcca    42840
ccaacctgtg cgacctttt  caattgacgc ggctttaagc gtttctttca ttacacgctc    42900
agtaaaaccc gctaagtaac cgttagacaa accttccaat cctggagcaa gagacccttt   42960
gttctgctct gttgttttta gaacttgcat tgttgcgtgc gctgcgactt tagcgttgga    43020
acttagtttt ggcattttgt taaccctcga acgatagtt  tttcttgtta agctgagcaa    43080
taatttcagc ttcagaaccg tggaacacct ctaggagccg accgtaactg ttgtaaacgt    43140
gcgcacagcg tccaggaatg caattcaggt agcgtgcctt tttgatttta cccttataca    43200
cagtgcaacc ctgattgcgg ttgctatgtg ttggtaagcg agtgatttgc gccattttgt    43260 taaccctat  taagtaagtg gggtaactat aacaagctac cccacaaagt tctagacaat    43320
gttaaaacgg aatgtcgtat tcccaactgt tacaaccctg accacatact ttcattggtg    43380
gcgttgcgtt gtacaacttg catatgttgt gttcatggtc cgcgtgcccg cagttagaac    43440
aattctgtaa cacgcccgcg tccatcatta gcttctgtgt tacgataact tcctgcttag    43500
aacgaaataa caggggtagt ggcttctccg tcatattgac cctcataatc tatttgtagg    43560
atttgtggat aaggtttctt gttggtgtgt acacggatgt tgcgaggtgt acggcactca    43620
tcaaagcgtt gtgcagcgtc agcaatggtt tcaggtacgt tgtcgtcgca acctgtagct    43680
tcacgccacc agtcgcgcgc tttcttaccc gcgaaacctt cgtgctccaa gcatagaggc    43740
tgagtaaact tacgcaaacc agtatgataa gcaatttcca agtaatccgg tttacctgca    43800
cgtccaccct tgcgagtgaa gaacacacgg tcaactttga atatatgcac ttccggaggc    43860
ggtgcggact tcttagcgcg tgcaataagc tcatcagttc ccgctttagc tttgaacttg    43920
atctcaggtg ggtactccgt accacactta ggacagaacc ttagcgacgc gtgcatcata    43980
aagttacact tatcacaaat gcgaacaggt gcttcaccac cacctttctt tttcttctcg    44040
ggtgtaacag ggtcgttaat cggtcctaag cgttgggtgt tacccgcaaa gtccaaaaca    44100
aggcaatcgg gttttaaact gttagcaatt gcgtcaagtc taccctgttg cgttgataaa    44160
tcgtaaccct ctgcgtaatc tgtacgtgta ccgcgaccaa gtatttgcac ccatagcgaa    44220
gctgattcag tagctcgaag aatacctagc aaatccacaa acggagcatc aaaaccagta    44280
gttaacacac ccatgttgac aagcgcggta actttcttgt ccataaacag cttaatgttt    44340
tcatctcgct gcttagaact catcttactg tgcacagcta ccgcagtgta accctgctca    44400
ataatttccg tgacaatgtg gtcacagtgc tcaacacccg ttgcaaagat tagccagtgc    44460
tcgcgtcctt ggtcctccgc tgcacgaacc atctccgcaa ctgctgcatg tgtaatctct    44520
```

-continued

```
tccttatccg tagcttttg aagttgcgac tgtacaaagt caccccttg tttacctaca    44580
cctttaaggt caatttcagt ttcagttcga tatggtgaca gggtgcacaa gtaccctga    44640
tcaaagaacc agttaaacgc atggaattca gttgcgtcaa ctaacacatg gtcgaagata   44700
cccatctcaa ggagtgtacc gccacccatt cggtaagctg tagcggttaa ccccaacaca   44760
atcattctag ggttcatctt cttaaggaac ttgataacct tctggtaact ggtgttcccg   44820
ctctttggta tacggtgaca ctcgtcaata attagcaagt caattttgcc gaactgccca   44880
gggttttga ccacactttg cacaccgcca aaagtgattg gatattgcgt gtccttacga    44940
cccgcacccg cagagtagat gcccgcaggt gcatgacgcc aaacagtctt tagcttgtcg   45000
tagttttgct caatcagctc ttttacgtgc gtgagcatca taacacgtgt tccaggccat   45060
tgcccgcaca tgcggcggac aatttcagca atgattatcg acttacctgt gcctgtaggg   45120
taaagcaaca daccgtcacc tttacccccg ttgcagtagt agtcaaagaa cgagttaatc   45180
ccgtactcct gataatctct aggcttcata cttcgtacca agctccttta gctcaacaga   45240
cgtgataaat cccggaccct gtttgaagtc ccgcccgctg cgagttctga gtacggtgta   45300
attgtcgtcc gtcgatccgc caacatggtc aaaggacggt agtaatgatg gatcaaacac   45360
gtgctcgggg caaccctgca tggcaagctg tttgtcgtgt acgtggttgt ttccacgtcg   45420
acatgaataa gagccattgg gttcagcact ccaatgacag cacgtgcgac agttgacatc   45480
tggaacttcc tttccgtggc agacgtcttt aacgtcacac caacgacatt tccaaaatgt   45540
aatcttatcg gagatgcgag ataccttacc ttcggcgaaa ataattgatc cagcgcgctt   45600
gctgtacttt tcagcaattt ctttatcata agtgataatt tctgcataca attcatccgt   45660
attcttgtta acaaccataa agagagtgta tggcaaattc atgtaatgca tacactgttg   45720
acactgtaca aagtaagtaa agttctcaat gcggcaaccg tctttaacga acttgttaaa   45780
cttactttca ctagcggttt taaactctgt gtaacacgcc gcgccttgtg gaacgtcggg   45840
aatacctagt gcaaccccgt ctaaagctga gccgtaatgc ccaccgtaat cactccattt   45900
aatttgaccc ccttcagggg tttcgtacca taactgaacg ccaggaatgc acattaacat   45960
tgacaagaaa cgcgcttcct ctaagtgtcc gcggttaaac agacgcagta agcgcggttc   46020
aaattttggt gctgctgtcc agcgccactt taattgaatt tcgcggtcgc attcgttacc   46080
gataccagat gcaccttggt ggttgcgaaa cttgtcttcc tgcccgcggt acgcgtcttc   46140
catcttagga aacaggtggc ggaggttcat gcggaattga ccacaattat ccgcagcgag   46200
tgcgttctca attgctttca gcgtttccgt tgcgtgctga acagggttcg caaaattggt   46260
tttaattcct accatgctcc tttatccttt atgacgcgct ttttaccacc tcggtaaaca   46320
gcttttgct tcttcttaga tttgtacaac tttagacgct ccttactcca tttgataacg    46380
tactcacatt cctcagcgtt aaactgacct atgtggcaat catcaaagtt aattttcata   46440
gatgctgcta gggatgcata agcgtgcacg cgtgagcaat acatgtaacg cttccagatc   46500
ttatcaaata cgtggtgtgc ttttgacgc atctttgcgg tgtgcttgtc gcacatgaaa    46560
cctttcgggt tgcgtgtacc ctcgtggcag gacacaaccg caccacacga agaacataac   46620
caaatgaaag gccagttacc tttctccgtg ccgtaaacga ccttatggtt tacgaactgc   46680
acgtggtcat ggttgcagtg gtgacagtgt gtaggttctg ggagttgttg acgctctaac   46740
atagtgttt tactttcctt attaacgaat acagggggta ttgtaacccc ctgtattaac    46800
ttatgctaga ctaggtcagc tgaattattg ctgagcccat ggtgggttgc caccttgtgc   46860
agcttgctga gcgtttggat cagactgcac ttggctagga ttaccctgac cgttgtcttg   46920
```

```
tacaggttgc tgatttacct gttgttgctg ctgttgctgt tgctgctctt gctgttgcgg   46980
agcgctgttc tgccaaggtt gttgctgaac ctcaccacct tgcggagctg cttcttgttg   47040
cgctgcttgc tgttgctgct gtacaggctg ctgtgcgttt ggatcttgcc actgctgctg   47100
ttgtactggc tgctgttgtt gctgctgctg tggtgcttgc tgttgctgct gcggtgcgtt   47160
ccattgctgc tgttgctgca ctggttgttg ttgctgttgt tgaccgccgt tccactgttg   47220
ttgtggtgca gcttgctgac cttgcgcggc aaagttctgc tgttgaccgc caaactgttg   47280
ctgaccgcca cccgcagcgt tcgcagtacg gtagcctttg atttcgttac gctgctcgta   47340
accgtcttgt ggtttagaca gaccaacctt cacttccatt gggataccgt gaagttgcat   47400
tgtgtcttgt agctgcatca cgttagttgc gtgacagata gcagacagtg tgcgctgtgc   47460
aatttcaacc gcagtttggt tcgggttgtt taggttcaag cgatcccaaa gcttacgacc   47520
tgcgtactgc tgaggtgcaa taacttcaag tgttagcagg atgtgtgaac cgttgttaga   47580
actgttcggc ttctcttctg agtcaacgat gcgtgcaacg taccaaccaa gcggcaagtt   47640
ttcaaaagcc tcgtttggag aaacttggtt agcgtcgaac atcgcgccaa gacctgcgcc   47700
agtaccgatt gaagaaagaa ttgctacagt aagtgcttta agtttcatgg atatatccta   47760
ttattgctgt ggttgagctt gcgagcccaa gattttgttg ataacgctac caatatgtgg   47820
gaactcaatt tcgtccagtg caccagaacg gtcttttgcg tccgcgctga agtctggttg   47880
agttcgcaga gctcggtaag aactctggtc gggattgcga ccgctaaaga gttggaacac   47940
ctcatccgtt agataagggg aagctgggcc aagcttctgt ccaggaacgg aaggacctgc   48000
aagggttaga cctgtaccct catccttgtt acgttcttct ttaaacagta acaccacatg   48060
tttcccgtct aggtcacgga agctttttaat tacttccaac atgcgttcaa gcattacacc   48120
gtaagcttga cgtggatctt ttgcacccett tttagcgtgc gcaagaactt tttctgccac   48180
ttcgctaaca gagtcaacaa tgattgtttg aaactgctgt gcttgtgggt tagtgcgaca   48240
gtaagcctca gcttcaatta agtcgtcaat tgtctcaatt tgaataactg gcagctcgta   48300
agtaatgccg ggcgtgttaa cacccccaaac acgctcaatg ttctcttttct taagagatag   48360 cagaccgcgc tctgcgctga tgattagcgg tgccggtgcc gtacagctga gcatggtctt   48420
acccataccc gaacgtccgt aaatggacat tttaacaccg tttgcaactg ctaacatatt   48480
tgaagattct agttggattg ccatttaaca actccggtta ggttagggag tacatagtac   48540
ccccaccgca ccaattaagc aagattttc agtagctctt ccaaaccacc tttgtccaag   48600
tttaactcgg tcataagggt ttcaagtgca cgtgttttct gtgcttcacg ttgcaactct   48660
tcaactttct cagttgcagc gtcgtcctta gctagaaggt cgtcgtaggc tttgcggtca   48720
accttagcaa caatccattt gtaacggaat ggtgcttcaa tgtcaatctt agctgttgtg   48780
tgaacgtcag tgaccacaac tactgtcata cctgtgcttg gcgcatccac aaccacttcg   48840
tcaccagctt ccaacttcat gtcttttgga gctttgtacg tgtacgcctg accaacagcg   48900
ttgccgttgt ggtctttgaa acgcacgtta acagttacgc agttagcagc gacaagggtc   48960
attagagcga tagcagcatt gttttcata atcctccgg gatttgtttt ggttgaacgc   49020
ttgtttggta tgggtacata atacagtacc accgcaaata agctagatta cttagttaaa   49080
ttcatatagt gcactgagtt aatacactat agggatttaa ctgtgcgcta tggggtacat   49140
aataccgcac atagcacaca ttactagact aaatcgttaa cacttatcgg tccgcgcttc   49200
agctatacct tcaccaccgt tactatagga actttcgcgg agtaggttga tcattaagcg   49260
```

```
acactgagcg ttatctttac catcaaagta gaaataacca gtgtggtcac ctgtagcttt   49320
aaactgtaac cccgtttcaa gtaggtcggt aatcaggata tcctgcggac cccacgaatc   49380
agtcttgcgt gcaagcactt cctgtcggtc tagctcgcgt gctttaaaca cagcaatttc   49440
agcagactgt tcagattgcg ttaacgacgc gacacgtgca tgatcactag cgtctaacag   49500
ttttggcata gctgtggcag ctagtacacc aaggatgata ataacaatta ccagttcgat   49560
aagggtaaaa cctttattag atttcatctt tcttctcctt tggaggaaca atatcaagtg   49620
ttggtgactt aggcttagta acaagcgcgt cttccaactt ctcacggtct tccatactaa   49680 ggtcttttgaa acccttagca attagtgacg gggtaaactt aacagccttg tcaattacgt   49740
gctcaggtag gtctgggcgt agcaattcga acacagtagg atcgagcttg gtttcttcac   49800
cgcgcacata cttgagcaca taacccgcac ctagttcgtg cttgttagta ccgttttttag   49860 cgtcagggaa catcttctca gcaatttgct tacgctgttc catttccaca gttttaagct   49920
ctttcagcaa agcttggttc aacgaccatg cgtggatcat ttggtcgttt gtcatgtcag   49980
gtgtaaagtg agcaatctta ttgttcatca gggctctccg gtgcttcagg ctcagacata   50040
ggtggaaccc acgtaggcca atctgtttta agggtgcgac gaattacatc cgcgctgtgt   50100
tccatggtaa tcgtatcaaa ccagtcaata ccaccaccag tataaacatc caagtccatt   50160
gcgatttcaa tagcttcaac cgcagaacct ttcatagcca ttgcaccaag tgcaaactga   50220
cccccgctac caatagcggt acgttttttcg tactcgcgtt ccatgtgacc acattggtta   50280
tccggtccgc ggaaacctgt gtaaatcatg tttggaagtc ctggagttac gcgaacagct   50340
aaaacagtga agtcaccgtc aggcactgaa aagcgttgct cagtagcaat ctcacccaca   50400
gcccaatcaa caacttcgat aaagcttggt gcattacccg caacagtcag cactagaccg   50460
tagtcagggt agaagtaaag cttacgcgca aagcggtcgc tcgcatggtt gttggaagtc   50520
acttgcttat ccgtagcaaa caacttaccg tcaaaggctg ctgtggtcat tatagacgct   50580
ccaaagcttt ctcaagcaaa tctaggttct taaaattacc agttacacgc tgaccgttct   50640
tggttgcgta gtaaccgaac ttgctacgtg aaacggagta cgtaaccccg ttcgcagtaa   50700
tatgactagc taacttagcc aaggtcagcc tccttcacaa atgtaccgtc aatccattta   50760
ccaccacgat ctttaatctc atcgtaggca gtctccagag ctaactcagg ggtaacttcc   50820
attgcagcac acatggtaaa cagcaagctg aagaagttaa tgagtggttg tttaatatcg   50880
cgcttacgac caaccgccgc agctagtgca ccatgtgcag caaccaaacg acagaacgtc   50940
aagcccgcat cgtcgtcagg gtcacgtagg tacacgcttt ccatcaattg cacagggtct   51000
aaaccggaca tgtgcgcttg gataatacca acaaccgtct gatcaccaag gtcgtcaagt   51060
acagtaacag cttcaccttc agctagacgt acaaggttag cagcaaactc accctgctct   51120 tcttcaccctt ttacttgctg cgaaacaagc gtagcgccac caacaaaacc acgagcgtca   51180
gcccaagcaa caacctttac aattagttcc gcaagttgcg gagtagatac attagacaca   51240
ggaaacccct tttgtgtgtt tgtttattaa gtgtgtatat aatacccccgc gaacggggta   51300 tatgctagac tactcgccca aatataaata tgcttcacat cgagcttggt acttgtcacg   51360
catttccttc ttagtgaaag aacgaataac gtccatagct tccaagtgac gtaaagctgc   51420
gttaatgtgg tcttcaacac cgcgaccacc agtatccgcg aacaacttgc ttcgaccaac   51480
actgcgaaca attgcagcac gactcaccaa gccatcgcga tgtaactctt ctttgtatac   51540
ccgcttcaag ctacttgtta gagctgcata aggttgctca acaaacttct gcataacact   51600
agcaataagc tcggcgcgac gttgtgttgt accgtccatt gtaaccttac cactctgaac   51660
```

```
agcatcccag acaaggtggt tgtgacgtag cacatagtcc caagcccagt tcatatgctg    51720
ctcgcaaacc ttaggcatgg tagggttatc catcaccgca agcaatgcag atatcttcat    51780
taccttcagg ttagtacgtg tccatgttgc gttccaagca tgggacgtat tttgttggtt    51840
caccatgtcc gtacagtaac gcgacagtgt gcggaacttt tcagaaatgt ccggaggtag    51900
cgcaatcggc ataacgtcca catggtttgg gtcacgcaat gcagagctca tacaaagcac    51960
agcgttagtc atgtggtcaa ttagagcggg actaggtcgc acacccttat caatgttatc    52020
gtatggcact tccccactaa actctgagaa gataaagcgc gatacaaaac cgtcaccaaa    52080
cgcctcttcg tttagacagt cgtagaacgt ttctggtaca cattctccaa ggaagctata    52140
agcaaccgca tggttaatgt taaccgtttt gtccatgtcc gtgtagcgaa caccacctag    52200
cacatcatac gcaccagact tagagtacgt ttcaaccata agatcacgca cagtacgggt    52260
agaaccgtca gggtttacca ttgcacggaa gtgattacca aactctgata aagcgtgcaa    52320
gaaagatgta ttctcttgga acactttcat catagagtta cggtgggtaa aggcttcact    52380
aaccacaaac ttgcttgcat caattacgcc ttgctcacgc tccaacaggc gcataaactc    52440
ttgaggtgct gctgttagct gtgacttacc agtaccggac ggagccaaca ccataaagta    52500
gttattgaga cccgttccgc taatgttgta agcgcgacca aacaaaccag acgcaaggga    52560
tagggcttct gcaatagcaa actccttaat ctgcttcaca cctgtgttgt aaaagtgctt    52620
cgcaagttcc cccatccatc caggcgggta ttgaagcttc ccttggagcg gtggcatctg    52680
gtactttggc tcagcgttac ccgtttgcgc gttggtattg cgcttcgcgt gtaactcttt    52740
tgcgagttta gcaccttcct cagcgtgggc tttgcgtaac tcttcgtctt tcatgttctc    52800
agtcgccgct tgtttaatag ctaagtgtaa cagacggtcg cttccaacat ggttgcgctt    52860
ctcgtgctgc ttcttacggt tgccgggata gcgaagctca agattagcaa gtgcagacat    52920
gcgccacaag cgtttacact gttcaatgtt gcgtgtgtag tacgttacaa ttgtcataaa    52980
cgcactgtca gcacgcgagg catcaaacac atccacgcca tgtgcaccct gctgcttcat    53040
aatctcaagg tacttgtccc aatcacccgt cataaggcat tcaaacttac cactgtggtc    53100
atatgcgtaa acctcagtaa gcaaatcagc atcgctcatc ttctcaggtt catcaatgtc    53160
cgcaatgttg tctaccttac gggaattcga gatatattgg ttaaactgat ctataagtcc    53220
aggatcgtaa cgaatgtcat atccaagaat aacattaccc gtacagataa tgaaacgttc    53280
cttggagtat aactctagtc caccacgttt gtatgaaccc gcaatctcac ctccaaacca    53340
taagtgatag ccccccaccgg aacgggaagc ctccgtatag gtttggtaag actgcacagc    53400
attccaccat tgctcagtag cttcaacacc agtatcatcg ccaatatcaa tgtccgctac    53460
tgtgaacccg tcaccctgtg taaggacaaa gccaaacccg cgttcagggt gttgctcaag    53520
caagggtaaa agttcttcat aactaactag cttattgtgg tcactagtta ccgaaatcgg    53580
gacgaactta ccgtccacat aagcaaacgg agccttagcc atcccgccgt caaactctgt    53640
gcctgtaaag caccaacgac gcagcttctt cagctgccaa ggcatatcca tctacttaac    53700
ctcgcatctt aatccaagct tgaataaact ccatcatgtc atcagtacgt ttccagtacc    53760
aagagttgcc aatcttaaat cgaggatact tgcgaagctt gttagtaacg ctaacagggg    53820
taacatcaac catctggcaa atgtcagcaa cggaaatata gagggcgtta ataactcct     53880 ggccatcata cttctcgcgg atgaatgtta gcatgtcttg ttcgctcatg ctcggcattg    53940
ccatgtcaga acccatacca cgctcgaacg gttgttccgt tgtacctact acattattgt    54000
```

| | |
|---|---|
| ttacagctac cattgtttgt tcctctttgc gttcaatgta tgcgctttat tatatgcata | 54060 |
| cgcctttaat taacaagaca accctatact ttattgtgac cacatacctg tcagctataa | 54120 |
| gcaatgcgta gagtaccggc tatgctttat aatacttgtc tttacaatgc acagagtacc | 54180 |
| tgcctggcaa gaccatgcgc tttactaata atgtgcagag tattgggact gcgtatacgg | 54240 |
| gttgtgcttt atatattatg tgcagagcac tggtactaca agacatagct tattgaaggg | 54300 |
| taactgaaag tgtgtattat agctaataag cagagtttat gtttattgcg ttactttctg | 54360 |
| ttgggaatat agtttgctgt tcttagctat atatagcgca ctgctagaag gtctactgag | 54420 |
| tgtatatagt taatagatac aacttacttc taataaaaaa gtagtgcgca attcaggggt | 54480 |
| cgaataccca atcgcatgta cactaacttt gttatgtaaa acagtaactt acccaagtt | 54540 |
| accaaagtta ccaaaaaaac gaagggggg gggatctgtg gatatctcta ggcccctcaa | 54600 |
| aactgtgcca gttgcgcact actttctagt ccaactagta gtaaaataaa agcatctaat | 54660 |
| agtaaattaa agttccaata aataaaatat ataataataa taataatgtc ttttaattta | 54720 |
| actactatat atatatgctt tattaagaac aattcaattg gtattactat ttaagtgttt | 54780 |
| taacggactt aatgctagta gtgtgcaaaa aagttgtgcc acttgtgcaa aaatggcttg | 54840 |
| actttgggta acaactagta atagcaatat atagtaacct taatttcgga ctcagtttga | 54900 |
| cgagttgtct gacaaacgca accaaaaagg tatttgaacg atgaaagtag caacaattga | 54960 |
| atataaagac gtagagccgg ggatgaacca atatctgaaa gttgttcgcg aaacgcccat | 55020 |
| cggtgaaacg cccacaggcg gaggtgaaac gccctgcaat gattctgtgc aatacggtgt | 55080 |
| ctatccgcaa atcaaattcc tgcgctttgc agaacgattt gaaatactag agcacgacat | 55140 |
| gggtacggtt ccttatgaac tcattgagca agggaattac tttggcgcag aagttgatat | 55200 |
| gtacgttagc ccagagcttt tggatttgct gcacgcttac aaaagagacc atgttgaaca | 55260 |
| tctaaaacaa caatgggcaa tggaaataaa caacgttaca gtcgcacaag gcaagttacg | 55320 |
| acgcgccaaa gaacaaattg aaacattgaa atggggttgc ataacattgg cagttgttgc | 55380 |
| gtcggggacg gttgcggcac ttggctatgt ggtcacacga atttaaaaaa ctggcaaatg | 55440 |
| aaaaaactgg cggttcgcta tagccagaag actggcgagc cgttgccttc cctctgatta | 55500 |
| cctttctta gctgttttag attatatttc tttagaagtg tgatgtgcag cgatatcccg | 55560 |
| accgcacccc gaaaaggtgt acattgcgaa tagcttggct cgcaagattc cgagtcgctg | 55620 |
| tatgcgcgtg tgcgcggctt tgtgcgctga tcaatgcaat ggtattggct agggtgctaa | 55680 |
| agtggcccac acgcgatttt agcgtgcttc attcggggta gctgcattta tatatagtgt | 55740 |
| gcgtgcgcgg ttacactagg taaagactaa aagcaaggat tatatcaccc gtttagttca | 55800 |
| ttaattcatg ataatgcgac attgcgcaca cttttaaacg gattgtgact ttttggtat | 55860 |
| ttttcgcaaa aattcgcttt acaggtgagt gaatatttcg cagtatgtac acacagcaac | 55920 |
| ggggtacagc aataaagcaa aaccccacta tataaaggt aatattatgt ctaaactaac | 55980 |
| aactacttca gcagttcgtg cacttcgtaa agcagctaaa tcagcaggtg ttcaagttgg | 56040 |
| tcgaatcgca atcagtgacc gcaccgaagt cggccttatc gacaacacca ccaaaatgtg | 56100 |
| gtcaggtcgc gttcagctgc actggtgcaa gggtagcgtg gaactaatgc agcgttattt | 56160 |
| agaaaacact aatttagttc ttaatgctcg accatgcggt gacggtcact tctctgtgtc | 56220 |
| tgttaacgta gcgtaacagg gttgttatac agtgcgccct acggggtgca ctaataacca | 56280 |
| tcttgttaat aatacctaaa gggggtaattc actatgtcaa ctatcaaaac atacgctaac | 56340 |
| aaatctggtc taatcaaagc gcttcgtcgt gcgggtgttg cggacgctga ccacatgcca | 56400 |

-continued

```
cagcaaaacg ctgagggccg ttggttccaa ggaactccga aggtcgtcat tcctaacgtt    56460
gttaactcgg ttgctgtgct gcgtggtgta gcattaccat gcgaagcacc taaaacggtg    56520
aagctatttg gtcgcggtat caagattgag aaaaaccgtg aagagaagaa tggcatcaaa    56580
cgacctagcg taggcggtgc gtgtcgcgct gtgtgggacg aatgtgaccg catctatgct    56640
gaaacgggtc tagtaccaat gccgaagcag cttaaagcgt gggcgcgtga ggtgggtgct    56700
aacgaaaaca acgcagtcat cgagctgtac gtgtggcgca agtttgaggg tcacactaaa    56760
tctaaagctt aatgtgccgc tttctggtgc gcatggttct aatcgctgta ctgtgcgcgc    56820
taatcccaat agcagcttat ttcttcataa tcttattatt tatggttcgt aaaccggagt    56880
cttaattatg tcacgtatca ctaaaaacga cctagaaatt gcaattgata atattaaccg    56940
cttgctcgcg cttaaaaaca gcgacacgcg cttccagcgt ggtgctgaaa acggtatgca    57000
ccacgttaaa gaatttgtca acggtcagta ccgttgtaat cgcagtgtgg gcacagctcg    57060
cgaagtgcat acatggttat gcggtgttca atacggttta acagcttaaa ggggtttatt    57120
atgccaaatg ttattaacgt tgaaaatcgc atcgaggttc gcgattggtt cactgcacaa    57180
cttaaagtgc aaggcatctc ttattgcaga ctgtacagca ataaagctcc caagcatcca    57240
aaagctgtac acgggtatcg tatgaagtat tacgccgtaa agcgtgacaa acacaaaaac    57300
gtaccaattc ttactcgctt ggaatttatc aacgctaaat ctcgcgcggt tggtatacct    57360
tttgcattgg agcgtgactt gggtcttaac gcttaccttc acacagtgca aagcttgcga    57420
attgtccctg taagcgactg tgcggttgat tgaccttcac cttgctctta gtattgatct    57480
tgcgctaacg tcgcaaatca acttatccac agaagttcaa ggtgcgcgta cagcgaattc    57540
ccgtacatgt ggtcataagc tgtacgtcct tgtggataac ctgtttagaa ctttcattac    57600
aaaagtgtgc actactgcac acttttttcg ttgacattac cccgaataat tcataatata    57660
agtacatacc aaacggggta acacacaaac ttatcggaga tttattatgt cactttcagc    57720
aacactatta agtattgtta accattcac tagcaacgct cagcaagttg gtgaagtagc    57780
tgatacgctt gtggcagctg atcagctaac aacccgcaca tacgttaact tgcgttcacg    57840
tgtagttcag cagctaatac gcaatcacgg gtacgaacta cttaatcacc acattggtga    57900
aggtactgtt agtgctaagt tgcaagcacc acatggtaca cgcttttggc tagtgttcag    57960
caacactgat gaatttacaa tcggggtgga ttacgcatgt taacactatt gttctttata    58020
ttatttttcc ctgtagctgc actgattggt gcggtattca acctcgatga aaagttagga    58080
taggagttat tcacatggat attaataaac tttgttatgt caaacccgca cttgaggagc    58140
tgttgcaagc gtacaattgg aagcgctgcg aacacactgg tatgctggaa acacttgact    58200
atgatgagga aaccctactt gatgatgtgt ttaacagtat cgaggtgtgc tgtacgggtg    58260
cgatgaggca ccgcgtgagt gacatggtga ccacgtgggt gctgtgcgac agcttactaa    58320
cactcgagga ccatagtggt ctactgttca tacattacac aacaggtgag gaagtggacc    58380
gacctgcata actatgcact aagcaataac cataccaaca aagcacgctt cggcgtgctt    58440 ttttttgtcga tgtcgttagc tattgttctt attgtgaaca acagctttat gctgtgcgta    58500
cagcgatccg ttcattgtgg aagtattcgg tgtacatgcc ccgaaggggt gggggtgcc    58560 acgatgggcg gctttttatg gaggccggag atgccgcatc gattatttat ttcctcagat    58620
atgtttcacc ctgtatatac atacagtatg accgatgtac agcttatcga tgtgtgtaca    58680
gctttgaggg gtatatcata ctcttcggtg tacatagggc gatgacctgg acgtgccgcc    58740
```

-continued

```
ggggggcccga  tgatcgtcga  caatatatgt  cggccgagat  ggtgacaact  ttatccgccg  58800
tccaaaaaga  tttgaggttt  tagaatgttg  tctagtaatg  tgctgcacac  tttgtataat  58860
gtacatactt  tctgcaacaa  cataaggtct  acatgatgga  aatagctaac  gaagaagtgc  58920
ttcaatacat  tgagtggtat  gaagcaacat  accctgaata  tgatcagtgg              58970
```

VIBRIO PARAHAEMOLYTICUS BACTERIOPHAGE VIB-PAP-5 AND USE THEREOF FOR SUPPRESSING PROLIFERATION OF VIBRIO PARAHAEMOLYTICUS BACTERIA

CROSS-REFERENCE TO RELATED APPLICATIONS

This application is a U.S. National Phase Application of International Application No. PCT/KR2017/006116, filed Jun. 13, 2017, which claims priority to Korean Application No. 10-2016-0073528, filed Jun. 14, 2016, each of which are hereby incorporated by reference in their entirety.

REFERENCE TO SEQUENCE LISTING

The Sequence Listing submitted Dec. 19, 2018 as a text file named "08162_0046U1_Revised_Sequence_Listing.txt," created on Dec. 19, 2018, and having a size of 77,824 bytes is hereby incorporated by reference pursuant to 37 C.F.R. § 1.52(e)(5).

TECHNICAL FIELD

The present invention relates to a bacteriophage isolated from nature, which infects *Vibrio parahaemolyticus* to thus kill *Vibrio parahaemolyticus*, and a method for preventing and treating a *Vibrio parahaemolyticus* infection using a composition including the same as an active ingredient. More particularly, the present invention relates to a Myoviridae bacteriophage Vib-PAP-5 (Accession number: KCTC 13029BP) isolated from nature, which has the ability to specifically kill *Vibrio parahaemolyticus* and which includes a genome expressed by SEQ. ID. NO: 1, and a method for preventing a *Vibrio parahaemolyticus* infection and a treatment method after the *Vibrio parahaemolyticus* infection using a composition including the bacteriophage as an active ingredient.

BACKGROUND ART

*Vibrio parahaemolyticus*, belonging to the genus *Vibrio*, is a gram-negative *bacillus*, and is known as a highly pathogenic bacterium that inhabits seawater or seafood and causes acute food poisoning and enteritis in human. The serotype of *Vibrio parahaemolyticus* includes three types of antigen, namely a flagella antigen (H), a somatic antigen (O), and a capsular antigen (K). Among them, the flagella antigen is present in all *Vibrio parahaemolyticus*. Therefore, the serovar of *Vibrio parahaemolyticus* is classified depending on the type of the somatic antigen and the capsular antigen, and 13 types of somatic antigens and 75 types of capsular antigens of *Vibrio parahaemolyticus* are known at present.

*Vibrio parahaemolyticus* cause serious economic damage in the aquaculture industry by causing vibriosis in various fishes and shellfishes. In particular, the outbreak of vibriosis in fish caused by a *Vibrio parahaemolyticus* infection occurs frequently, resulting in great economic damage. Therefore, there is an urgent need to develop a method that is applicable for preventing and further treating a *Vibrio parahaemolyticus* infection.

Antibiotics are extensively used for the inhibition and treatment of infections caused by *Vibrio parahaemolyticus*. Recently, the effectiveness of antibiotics has been continuously decreasing due to the increase of antibiotic-resistant bacteria, and the development of effective methods other than antibiotics is required due to the increased number of regulations on the use of antibiotics in cultured fish. Especially, there is a great demand for environmentally friendly methods.

Recently, the use of bacteriophages as a countermeasure against bacterial diseases has attracted considerable attention. In particular, interest in bacteriophages is higher than ever due to the preference of environmentally friendly methods. Bacteriophages are very small microorganisms infecting bacteria and are usually simply called "phages". Once a bacteriophage infects bacteria, the bacteriophage is proliferated in the inside of the bacterial cell. After proliferation, the progeny of the bacteriophage destroys the bacterial cell wall and escapes from bacteria as the host, suggesting that the bacteriophage has the ability to kill bacteria.

The manner in which the bacteriophage infects bacteria is characterized by very high specificity thereof, so that the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria and does not affect commensal bacteria in the environment or in the intestines of fish. Conventional antibiotics, which have been widely used for bacterial treatment, influence many kinds of bacteria coincidentally. This causes problems such as environmental pollution or the disturbance of normal flora in animals. On the other hand, the use of bacteriophages does not disturb normal flora in animals, because the target bacterium is killed selectively. Hence, the bacteriophage may be utilized safely, which thus greatly lessens the probability of adverse actions in use compared to any other antibiotics.

Bacteriophages were first discovered by the English bacteriologist Twort in 1915 when he noticed that *Micrococcus* colonies melted and became transparent by something unknown. In 1917, the French bacteriologist d'Herelle discovered that *Shigella dysenteriae* in the filtrate of dysentery patient feces was melted by something, and further studied this phenomenon. As a result, he identified bacteriophages independently, and named them bacteriophages, which means "to eat bacteria". Since then, bacteriophages acting against such pathogenic bacteria as *Shigella, Salmonella Typhi*, and *Vibrio cholerae* have been continuously identified.

Owing to the unique ability of bacteriophages to kill bacteria, bacteriophages have attracted anticipation as an effective countermeasure against bacterial infection since their discovery, and there has been a lot of research related thereto. However, since penicillin was discovered by Fleming, studies on bacteriophages have continued only in some Eastern European countries and the former Soviet Union because the spread of antibiotics was generalized. Since 2000, the limitations of conventional antibiotics have appeared due to the increase in antibiotic-resistant bacteria, and the possibility of developing bacteriophages as a substitute for conventional antibiotics has been highlighted, so that bacteriophages are again attracting attention as antibacterial agents. In particular, recently, government regulations for the use of antibiotics have become more stringent around the world, and thus interest in bacteriophages is increasing and industrial applications therefor are increasingly arising.

As demonstrated above, bacteriophages tend to be highly specific for bacteria. Because of this specificity, bacteriophages frequently exhibit an antibacterial effect only for certain strains of bacteria, even though the bacteria belong to the same species. In addition, the different bacteriophages exhibit different antibacterial strengths against the same bacteria strain. Therefore, it is necessary to collect many kinds of bacteriophages that are useful to control specific bacteria efficiently. Hence, in order to develop the effective bacteriophage utilization method in response to *Vibrio parahaemolyticus*, many kinds of bacteriophages that exhibit antibacterial action against *Vibrio parahaemolyticus* must be acquired. Furthermore, the resulting bacteriophages need to be screened as to whether or not they are superior to others from the aspect of antibacterial strength and spectrum.

DISCLOSURE

Technical Problem

Therefore, the present inventors endeavored to develop a composition applicable for the prevention or treatment of a *Vibrio parahaemolyticus* infection using a bacteriophage that is isolated from nature and can selectively kill *Vibrio parahaemolyticus*, and further to establish a method for preventing or treating a *Vibrio parahaemolyticus* infection using the composition. As a result, the present inventors isolated a bacteriophage suitable for this purpose from nature and secured the gene sequence of the genome that distinguishes the isolated bacteriophage from other bacteriophages. Then, the present inventors developed a composition including the bacteriophage as an active ingredient, and identified that this composition could be efficiently used to prevent and treat a *Vibrio parahaemolyticus* infection, leading to the completion of the present invention.

Accordingly, it is an object of the present invention to provide a Myoviridae bacteriophage Vib-PAP-5 (Accession number: KCTC 13029BP) isolated from nature, which has the ability to specifically kill *Vibrio parahaemolyticus* and which includes the genome expressed by SEQ. ID. NO: 1.

It is another object of the present invention to provide a composition applicable for preventing *Vibrio parahaemolyticus* infection, which includes a bacteriophage Vib-PAP-5 infecting *Vibrio parahaemolyticus* to thus kill *Vibrio parahaemolyticus* as an active ingredient, and a method for preventing a *Vibrio parahaemolyticus* infection using said composition.

It is another object of the present invention to provide a composition applicable for treating a *Vibrio parahaemolyticus* infection, which includes a bacteriophage Vib-PAP-5 infecting *Vibrio parahaemolyticus* to thus kill *Vibrio parahaemolyticus* as an active ingredient, and a method for treating a *Vibrio parahaemolyticus* infection using said composition.

It is another object of the present invention to provide medicine bath agent (immersion agent) for preventing and treating a *Vibrio parahaemolyticus* infection using said composition.

It is another object of the present invention to provide a feed additive effective upon farming by preventing and treating a *Vibrio parahaemolyticus* infection using said composition.

Technical Solution

The present invention provides a Myoviridae bacteriophage Vib-PAP-5 (Accession number: KCTC 13029BP) isolated from nature, which has the ability to specifically kill *Vibrio parahaemolyticus* and which includes a genome expressed by SEQ. ID. NO: 1, and a method for preventing and treating *Vibrio parahaemolyticus* infection using a composition including the same as an active ingredient.

The bacteriophage Vib-PAP-5 was isolated by the present inventors and then deposited at Korean Collection for Type Cultures, Korea Research Institute of Bioscience and Biotechnology on May 26, 2016 (Accession number: KCTC 13029BP).

The present invention also provides a medicine bath agent and a feed additive applicable for the prevention or treatment of a *Vibrio parahaemolyticus* infection, which include the bacteriophage Vib-PAP-5 as an active ingredient.

Since the bacteriophage Vib-PAP-5 included in the composition of the present invention kills *Vibrio parahaemolyticus* efficiently, it is regarded effective in the prevention (prevention of infection) or treatment (treatment of infection) of diseases caused by *Vibrio parahaemolyticus*. Therefore, the composition of the present invention can be utilized for the prevention and treatment of diseases caused by Vibrio parahaemolyticus.

In this description, the term "prevention" or "prevent" indicates (i) to block a *Vibrio parahaemolyticus* infection; and (ii) to inhibit the development of diseases caused by a *Vibrio parahaemolyticus* infection.

In this description, the term "treatment" or "treat" indicates all actions that (i) suppress diseases caused by *Vibrio parahaemolyticus*; and (ii) alleviate the pathological condition of the diseases caused by *Vibrio parahaemolyticus*.

In this description, the term "isolate", "isolating", or "isolated" indicates actions which isolate bacteriophages from nature by applying diverse experimental techniques and which secure characteristics that can distinguish the target bacteriophage from others, and further includes the action of proliferating the target bacteriophage using bioengineering techniques so that the target bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Vib-PAP-5 is included as an active ingredient. The bacteriophage Vib-PAP-5 is included at a concentration of $1\times10^1$ pfu/ml to $1\times10^{30}$ pfu/ml or $1\times10^1$ pfu/g to $1\times10^{30}$ pfu/g, and preferably at a concentration of $1\times10^4$ pfu/ml to $1\times10^{15}$ pfu/ml or $1\times10^4$ pfu/g to $1\times10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. The formulation may be in the form of a solution, suspension, or emulsion in oil or a water-soluble medium, extract, powder, granule, tablet, or capsule. A dispersing agent or stabilizer may be additionally included.

The composition of the present invention may be prepared as a medicine bath agent or a feed additive according to the purpose of use, without limitation thereto.

For this purpose, bacteriophages that confer antibacterial activity against other bacterial species may be further included in the composition of the present invention in order to improve the effectiveness thereof. In addition, other kinds of bacteriophages that have antibacterial activity against *Vibrio parahaemolyticus* may be further included in the composition of the present invention. These bacteriophages may be combined properly so as to maximize antibacterial effects, because their antibacterial activities against *Vibrio parahaemolyticus* may be different from the aspects of antibacterial strength and spectrum.

Advantageous Effects

The method for preventing and treating *Vibrio parahaemolyticus* infection using the composition including the bacteriophage Vib-PAP-5 as an active ingredient according to the present invention may have the advantage of very high specificity for *Vibrio parahaemolyticus*, compared with the conventional methods based on chemical materials including conventional antibiotics. This means that the composition can be used for preventing or treating the *Vibrio parahaemolyticus* infection without affecting other commensal bacteria that are useful and has fewer side effects according to the use thereof. In general, when chemical materials such as antibiotics are used, commensal bacteria are also damaged, thus weakening immunity in animals and entailing various side effects owing to the use thereof. Further, the composition of the present invention uses a bacteriophage isolated from nature as an active ingredient, and thus it is very environmentally friendly. Meanwhile, in the case of bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to *Vibrio parahaemolyticus*. Typically, bacteriophages are usually effective only on some bacterial strains, even within the same species. That is to say, the antibacterial activity of bacteriophage may depend on the bacterial strain even for the same species of bacteria]. Accordingly, the present invention may provide antibacterial activity against *Vibrio parahaemolyticus* different to that provided by other bacteriophages acting on *Vibrio parahaemolyticus*. This provides significantly different applicability to industrial fields.

DESCRIPTION OF DRAWINGS

FIG. 1 is an electron micrograph showing the morphology of the bacteriophage Vib-PAP-5.

FIG. 2 is a photograph showing the results of an experiment on the ability of the bacteriophage Vib-PAP-5 to kill *Vibrio parahaemolyticus*. The clear zone is a plaque formed by lysis of the target bacteria.

MODE FOR INVENTION

Hereinafter, the present invention will be described in more detail with reference to Examples. However, the Examples are merely examples of the present invention, and the scope of the present invention is not limited to the Examples.

Example 1: Isolation of Bacteriophage Capable of Killing *Vibrio parahaemolyticus*

Samples were collected from nature to isolate the bacteriophage capable of killing *Vibrio parahaemolyticus*. Meanwhile, the *Vibrio parahaemolyticus* strains used for the bacteriophage isolation had been previously isolated and identified as *Vibrio parahaemolyticus* by the present inventors.

The isolation procedure of the bacteriophage is described in detail hereinafter. The collected sample was added to an LB (Luria-Bertani) culture medium (tryptone, 10 g/L; yeast extract, 5 g/L; sodium chloride, 10 g/L) inoculated with *Vibrio parahaemolyticus* at a ratio of 1/1,000, followed by shaking culture at 37° C. for 3 to 4 hours. Upon completion of the culture, centrifugation was performed at 8,000 rpm for 20 minutes and a supernatant was recovered. The recovered supernatant was inoculated with *Vibrio parahaemolyticus* at a ratio of 1/1,000, followed by shaking culture at 37° C. for 3 to 4 hours. When the sample contained the bacteriophage, the above procedure was repeated a total of 5 times in order to sufficiently increase the number (titer) of the bacteriophages. After repeating the procedure 5 times, the culture solution was subjected to centrifugation at 8,000 rpm for 20 minutes. After the centrifugation, the recovered supernatant was filtered using a 0.45 μm filter. The obtained filtrate was used in a typical spot assay for examining whether or not a bacteriophage capable of killing *Vibrio parahaemolyticus* was included therein.

The spot assay was performed as follows: LB culture medium was inoculated with *Vibrio parahaemolyticus* at a ratio of 1/1,000, followed by shaking culture at 37° C. for overnight. 3 ml ($OD_{600}$ of 1.5) of the culture solution of *Vibrio parahaemolyticus* prepared above was spread on LA (Luria-Bertani Agar; tryptone, 10 g/L; yeast extract, 5 g/L; sodium chloride, 10 g/L; agar, 15 g/L) plate. The plate was left on a clean bench for about 30 minutes to dry the spread solution. After drying, 10 μl of the prepared filtrate was spotted onto the plate culture medium on which *Vibrio parahaemolyticus* was spread and then left for about 30 minutes to dry. After drying, the plate culture medium that was subjected to spotting was stationary-cultured at 37° C. for one day, and then examined for the formation of a clear zone at the position at which the filtrate was dropped. In the case of the filtrate generating the clear zone, it is judged that the bacteriophage capable of killing *Vibrio parahaemolyticus* is included therein. Through the above examination, the filtrate containing the bacteriophage having the ability to kill *Vibrio parahaemolyticus* could be obtained.

The pure bacteriophage was isolated from the filtrate confirmed above to have the bacteriophage capable of killing *Vibrio parahaemolyticus*. A conventional plaque assay was used for the isolation of the pure bacteriophage. In detail, a plaque formed in the course of the plaque assay was recovered using a sterilized tip, which was then added to the culture solution of *Vibrio parahaemolyticus*, followed by culturing at 37° C. for 4 to 5 hours. After the culturing, centrifugation was performed at 8,000 rpm for 20 minutes to obtain a supernatant. The *Vibrio parahaemolyticus* culture solution was added to the obtained supernatant at a volume ratio of 1/50, followed by culturing at 37° C. for 4 to 5 hours. In order to increase the number of bacteriophages, the above procedure was repeated at least 5 times. Then, centrifugation was performed at 8,000 rpm for 20 minutes to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for the isolation of the pure bacteriophage was generally repeated until the generated plaques became similar to each other in size and morphology. In addition, the final isolation of the pure bacteriophage was confirmed using electron microscopy. Until the isolation of the pure bacteriophage was confirmed using the electron microscopy, the above procedure was repeated. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage isolated above was confirmed to belong to the Myoviridae bacteriophage.

The solution containing the pure bacteriophage confirmed above was subjected to the following purification process. The *Vibrio parahaemolyticus* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% Gelatin, pH 8.0). The resulting material was referred to as a bacteriophage suspension or bacteriophage solution.

As a result, the pure bacteriophage purified above was collected, was named the bacteriophage Vib-PAP-5, and then deposited at Korean Collection for Type Cultures, Korea Research Institute of Bioscience and Biotechnology on May 26, 2016 (Accession number: KCTC 13029BP).

Example 2: Separation and Sequence Analysis of Genome of Bacteriophage Vib-PAP-5

The genome of the bacteriophage Vib-PAP-5 was separated as follows. The genome was separated from the bacteriophage suspension obtained using the same method as in Example 1. First, in order to eliminate DNA and RNA of *Vibrio parahaemolyticus* included in the suspension, 200 U of each of DNase I and RNase A was added to 10 ml of the bacteriophage suspension and then left at 37° C. for 30 minutes. After being left for 30 minutes, in order to remove the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After the reaction for 1 hour, 10 ml of the solution of phenol:chloroform:isoamyl alcohol mixed at a component ratio of 25:24:1 was added to the reaction solution, followed by mixing well. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the genome of the bacteriophage Vib-PAP-5.

Information on the sequence of the genome of the bacteriophage Vib-PAP-5 obtained above was secured by performing next-generation sequencing analysis using Illumina Mi-Seq equipment from Macrogen, Inc. The finally analyzed genome of the bacteriophage Vib-PAP-5 had a size of 58,970 bp and the sequence of the whole genome was expressed by SEQ. ID. NO: 1.

The homology (similarity) of the bacteriophage Vib-PAP-5 genomic sequence obtained above with previously reported bacteriophage genomic sequences was investigated using BLAST (ncbi.nlm.nih.gov/BLAST/) on the web. As a result of the BLAST investigation, bacteriophage sequences with homology of 50% or more were not confirmed.

Based upon this result, it is concluded that the bacteriophage Vib-PAP-5 must be a novel bacteriophage that has not been reported previously. Further, since the antibacterial strength and spectrum of bacteriophages typically depend on the type of bacteriophage, it is considered that the bacteriophage Vib-PAP-5 can provide antibacterial activity different from that of any other bacteriophages reported previously.

Example 3: Investigation of Ability of Bacteriophage Vib-PAP-5 to Kill *Vibrio parahaemolyticus*

The ability of the isolated bacteriophage Vib-PAP-5 to kill *Vibrio parahaemolyticus* was investigated. In order to investigate the killing ability, the formation of clear zones was observed using the spot assay in the same manner as described in Example 1. A total of 18 strains which had been isolated and identified as *Vibrio parahaemolyticus* by the present inventors were used as *Vibrio parahaemolyticus* for the investigation of killing ability. The bacteriophage Vib-PAP-5 had the ability to kill a total of 17 strains among 18 strains of *Vibrio parahaemolyticus* as the experimental target. The representative experimental result is shown in FIG. 2. Meanwhile, the ability of the bacteriophage Vib-PAP-5 to kill *Edwardsiella tarda, Vibrio anguillarum, Vibrio ichthyoenteri, Lactococcus garvieae, Streptococcus parauberis, Streptococcus iniae*, and *Aeromonas salmonicida* was also investigated in a separate experiment. As a result, the bacteriophage Vib-PAP-5 did not have the ability to kill these microorganisms.

Therefore, it is confirmed that the bacteriophage Vib-PAP-5 has the specific ability to kill *Vibrio parahaemolyticus* and a broad antibacterial spectrum against *Vibrio parahaemolyticus*, suggesting that the bacteriophage Vib-PAP-5 can be used as an active ingredient of the composition for preventing and treating *Vibrio parahaemolyticus* infection.

Example 4: Experimental Example Regarding Prevention of *Vibrio parahaemolyticus* Infection Using Bacteriophage Vib-PAP-5

100 µl of a bacteriophage Vib-PAP-5 solution at a level of $1\times10^8$ pfu/ml was added to a tube containing 9 ml of an LB culture medium. To another tube containing 9 ml of an LB culture medium, only the same amount of LB culture medium was further added. A *Vibrio parahaemolyticus* culture solution was then added to each tube so that absorbance reached about 0.5 at 600 nm. After *Vibrio parahaemolyticus* was added, the tubes were transferred to an incubator at 37° C., followed by shaking culture, during which the growth of *Vibrio parahaemolyticus* was observed. As presented in Table 1, it was observed that the growth of *Vibrio parahaemolyticus* was inhibited in the tube to which the bacteriophage Vib-PAP-solution was added, while the growth of *Vibrio parahaemolyticus* was not inhibited in the tube to which the bacteriophage solution was not added.

TABLE 1

Growth inhibition of *Vibrio parahaemolyticus*

| Classification | $OD_{600}$ absorbance value | | |
|---|---|---|---|
| | 0 minutes after culture | 60 minutes after culture | 120 minutes after culture |
| Bacteriophage solution is not added | 0.501 | 0.966 | 1.681 |
| Bacteriophage solution is added | 0.501 | 0.302 | 0.226 |

The above results indicate that the bacteriophage Vib-PAP-5 of the present invention not only inhibits the growth of *Vibrio parahaemolyticus* but also has the ability to kill *Vibrio parahaemolyticus*. Therefore, it is concluded that the bacteriophage Vib-PAP-5 can be used as an active ingredient of the composition for preventing a *Vibrio parahaemolyticus* infection.

Example 5: Animal Experiment on Prevention of *Vibrio parahaemolyticus* Infection Using Bacteriophage Vib-PAP-5

The preventive effect of the bacteriophage Vib-PAP-5 on sea bass subjected to *Vibrio parahaemolyticus* infection was investigated. A total of 2 groups of sixty juvenile sea bass per group (body weight: 5 to 7 g and body length: 8 to 10 cm) was prepared and farmed separately in water tanks, and an experiment was performed for 14 days. The environment surrounding the water tanks was controlled, and the temperature in the laboratory where the water tanks were located was maintained constant. Over the whole experimental period from the $1^{st}$ day of the experiment, sea bass in an experimental group (the group to which the bacteriophage was administered) was fed with a feed containing the bacteriophage Vib-PAP-5 at $1\times10^8$ pfu/g according to a conventional feeding method. In contrast, sea bass in a control group (the group to which the bacteriophage was not administered) was fed with the same feed as in the experimental group except that the bacteriophage Vib-PAP-5 was not contained according to the same method as in the experimental group. From the seventh day after the experiment started, the feed to be provided was contaminated with *Vibrio parahaemolyticus* at a level of $1\times10^8$ cfu/g for two days and thereafter provided respectively twice a day so as to induce a *Vibrio parahaemolyticus* infection. From the ninth day after the experiment started (the second day after the *Vibrio parahaemolyticus* infection was induced), vibriosis pathogenesis was examined in all test animals on a daily basis. The vibriosis pathogenesis was examined by measuring a body darkening index. The measurement of the body darkening index was performed using a conventional method for measuring a dark coloration (DC) score (0: normal, 1: slight darkening, 2: strong darkening). The results are shown in Table 2.

TABLE 2

Result of measurement of body darkening index (mean)

| | DC score (mean) | | | | | |
|---|---|---|---|---|---|---|
| Days | D9 | D10 | D11 | D12 | D13 | D14 |
| Control group (bacteriophage is not administered) | 0.72 | 0.72 | 0.76 | 0.80 | 1.00 | 1.08 |
| Experimental group (bacteriophage is administered) | 0.20 | 0.04 | 0 | 0 | 0 | 0 |

From the above results, it is confirmed that the bacteriophage Vib-PAP-5 of the present invention could be very effective in inhibiting *Vibrio parahaemolyticus* infection.

Example 6: Example of Treatment of Infectious Diseases of *Vibrio parahaemolyticus* Using Bacteriophage Vib-PAP-5

The treatment effect of the bacteriophage Vib-PAP-on sea bass suffering from vibriosis caused by *Vibrio parahaemolyticus* was investigated. A total of 2 groups of sixty juvenile sea bass per group (body weight: 5 to 7 g and body length: 8 to 10 cm) was prepared and farmed separately in water tanks, and an experiment was performed for 14 days. The environment surrounding the water tanks was controlled, and the temperature in the laboratory where the water tanks stayed was maintained. From the fifth day after the experiment started, the feed contaminated with *Vibrio parahaemolyticus* at a level of $1\times10^8$ cfu/g was provided twice a day for three days according to a conventional feeding method. Sea bass subjects showing clinical symptoms of vibriosis were observed in both water tanks from the last day of the procedure in which the feed contaminated with *Vibrio parahaemolyticus* was provided. From the next day after the feed contaminated with *Vibrio parahaemolyticus* was provided for three days (the eighth day after the experiment started), sea bass in an experimental group (the group to which the bacteriophage was administered) was fed with a feed containing the bacteriophage Vib-PAP-5 (1x $10^8$ pfu/g) according to a conventional feeding method. In contrast, sea bass in a control group (the group to which the bacteriophage was not administered) was fed with the same feed as in the experimental group except that the bacteriophage Vib-PAP-5 was not contained according to the same method as in the experimental group. From the third day after the forced infection of *Vibrio parahaemolyticus* (the eighth day after the experiment started), vibriosis pathogenesis was examined in all test animals on a daily basis. The vibriosis pathogenesis caused by *Vibrio parahaemolyticus* was examined by measuring a body darkening index as in Example 5. The results are shown in Table 3.

TABLE 3

Result of measurement of body darkening index (mean)

| Days | DC score (mean) | | | | | | |
|---|---|---|---|---|---|---|---|
| | D8 | D9 | D10 | D11 | D12 | D13 | D14 |
| Control group (bacteriophage is not administered) | 0.93 | 1.03 | 1.10 | 1.17 | 1.20 | 1.30 | 1.33 |
| Experimental group (bacteriophage is administered) | 1.03 | 0.93 | 0.87 | 0.77 | 0.43 | 0.23 | 0.17 |

From the above results, it is confirmed that the bacteriophage Vib-PAP-5 of the present invention could be very effective in the treatment of infectious diseases caused by *Vibrio parahaemolyticus*.

Example 7: Preparation of Feed Additives and Feeds

Feed additives were prepared using a bacteriophage Vib-PAP-5 solution so that a bacteriophage Vib-PAP-5 was contained in an amount of $1\times10^8$ pfu per 1 g of the feed additives. The method of preparing the feed additives was as follows: Maltodextrin (50%, w/v) was added to the bacteriophage solution and the resulting mixture was then freeze-dried. Finally, the dried mixture was ground into fine powders. In the above-described preparation procedure, the drying procedure can be replaced with drying under a reduced pressure, drying with heat, or drying at room temperature. In order to prepare the control for comparison, the feed additives that did not contain the bacteriophage but contained a buffer (10 mM Tris-HCl, 10 mM $MgSO_4$, 0.1% Gelatin, pH 8.0) used to prepare the bacteriophage solution was prepared.

The two kinds of feed additives that were prepared above were each mixed with a raw fish-based moist pellet at a weight ratio of 250, thus preparing two kinds of final feeds.

Example 8: Preparation of Medicine Bath Agent

The method of preparing a medicine bath agent was as follows: The medicine bath agent was prepared using a bacteriophage Vib-PAP-5 solution so that a bacteriophage Vib-PAP-5 was contained in an amount of $1\times10^8$ pfu per 1 ml of the medicine bath agent. In the method of preparing the medicine bath agent, the bacteriophage Vib-PAP-5 solution was added so that the bacteriophage Vib-PAP-5 was contained in an amount of $1\times10^8$ pfu per 1 ml of a buffer used to prepare the bacteriophage solution, and mixing was sufficiently performed. In order to prepare the control for comparison, the buffer used to prepare the bacteriophage solution was used as the medicine bath agent that did not contain the bacteriophage.

The two prepared kinds of medicine bath agents were diluted with water at a volume ratio of 1,000, resulting in the final medicine bath agent.

Example 9: Confirmation of Feeding Effect on Sea Bass Farming

Improvement in the feeding result upon sea bass farming was investigated using the feed and the medicine bath agents prepared in Examples 7 and 8. In particular, the investigation was focused on mortality. A total of 800 juvenile sea bass was divided into two groups, each including 400 sea bass (group A; fed with the feeds and group B; treated with the medicine bath agent), and an experiment was performed for four weeks. Each group was divided into sub-groups each including 200 sea bass, and the sub-groups were classified into a sub-group to which the bacteriophage Vib-PAP-5 was applied (sub-group-①) and a sub-group to which the bacteriophage was not applied (sub-group-②). In the present experiment, the target sea bass was the juvenile (body weight: 5 to 7 g and body length: 8 to 10 cm), and the juvenile sea bass of the experimental sub-groups was farmed in separate water tanks placed apart from each other at a certain space interval. The sub-groups were classified and named as shown in Table 4.

TABLE 4

Sub-group classification and expression in sea bass feeding experiment

| | Sub-group classification and expression | |
|---|---|---|
| Application | Bacteriophage Vib-PAP-5 is applied | Bacteriophage is not applied |
| Group fed with feeds | A-① | A-② |
| Group treated with medicine bath agent | B-① | B-② |

In the case of provision of the feeds, the feeds prepared in Example 7 were provided according to a conventional feeding method as classified in Table 4. The treatment using the medicine bath agent was performed according to a conventional treatment method using a medicine bath agent as classified in Table 4 using the medicine bath agent prepared as described in Example 8. The results are shown in Table 5.

TABLE 5

Mortality of sea bass in feeding experiment

| Group | Dead sea bass/total sea bass of experiment (No.) | Mortality (%) |
|---|---|---|
| A-① | 7/200 | 3.5 |
| A-② | 39/200 | 19.5 |
| B-① | 9/200 | 4.5 |
| B-② | 58/200 | 29.0 |

The above results indicate that the provision of the feed prepared according to the present invention and the treatment using the medicine bath agent prepared according to the present invention were effective in improving the feeding result in the farming of sea bass. Therefore, it is concluded that the composition of the present invention could be efficiently applied to improving the results of animal feeding.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

Name of Depositary Authority: KCTC
Accession number: KCTC 13029BP
Accession date: 20160526

The invention claimed is:

1. A method for treating a *Vibrio parahaemolyticus* infection, the method comprising: administering to an animal other than a human a composition comprising an isolated Myoviridae bacteriophage Vib-PAP-5 (Accession number: KCTC 13029BP) that can kill *Vibrio parahaemolyticus* specifically as an active ingredient, wherein the Myovirdae bacteriophage Vib-PAP-5 is prepared by bacterial culture with inoculum of bacteriophage Vib-PAP-5 and comprises a genome encoded by the nucleotide sequence of SEQ ID NO:1, wherein the composition is administered as a feed additive or a medicine bath agent.

2. The method of claim 1, wherein said composition further comprises a pharmaceutically acceptable carrier.

3. The method of claim 2, wherein said composition for the medicine bath agent comprises the bacteriophage Vib-PAP-5 at a concentration of $1\times10^1$ pfu/ml to $1\times10^{30}$ pfu/ml.

4. The method of claim 2, wherein said composition for the food additive comprises the bacteriophage Vib-PAP-5 at a concentration of $1\times10^1$ pfu/g to $1\times10^{30}$ pfu/g.

* * * * *